(12) United States Patent
Volpicelli et al.

(10) Patent No.: US 7,999,124 B2
(45) Date of Patent: Aug. 16, 2011

(54) PROCESS FOR PREPARING NEBIVOLOL

(75) Inventors: Raffaella Volpicelli, Vicenza (IT); Paolo Maragni, Virgilio (IT); Livius Cotarca, Cervignano del Friuli (IT); Johnny Foletto, Arcole (IT); Franco Massaccesi, Lonigo (IT)

(73) Assignee: Zach System S.p.A., Bresso (IT)

( * ) Notice: Subject to any disclaimer, the term of this patent is extended or adjusted under 35 U.S.C. 154(b) by 161 days.

(21) Appl. No.: 12/515,375

(22) PCT Filed: Nov. 23, 2007

(86) PCT No.: PCT/EP2007/010185
§ 371 (c)(1),
(2), (4) Date: May 18, 2009

(87) PCT Pub. No.: WO2008/064827
PCT Pub. Date: Jun. 5, 2008

(65) Prior Publication Data
US 2010/0056813 A1  Mar. 4, 2010

(30) Foreign Application Priority Data

Nov. 27, 2006  (EP) .................................... 06124837

(51) Int. Cl.
C07D 311/04 (2006.01)
C07D 317/22 (2006.01)
C07F 5/02 (2006.01)
(52) U.S. Cl. .......................... 549/407; 549/213; 549/453
(58) Field of Classification Search .................. 549/213, 549/407, 453
See application file for complete search history.

(56) References Cited

U.S. PATENT DOCUMENTS 7,560,575 B2 * 7/2009 Bader et al. .................. 549/407
2007/0021623 A1 * 1/2007 Parthasaradhi Reddy et al. ............................ 549/403

FOREIGN PATENT DOCUMENTS

EP 0334429 A 9/1989
EP 1803715 A1 * 7/2007
WO 2004/041805 A 5/2004

OTHER PUBLICATIONS

Chandrasekhar, et al., Enantioselective total synthesis of the antihypertensive agent (S,R,R,R)-nebivolol, Tetrahedron, 2000, 56:6339-6344.
Yu, et al., A Convenient Synthesis of 1-[6-Fluoro-(2S)-3H,4H-dihydro-2H-2-chromenyl]-. (1R)-1,2-ethanediol and 1-[6- Fluoro-(2R)-3H,4H-dihydro-2H-2-chromenyl]-. (1R)-1,2-ethanediol, Synlett, 2005, 9:1465-1467.
Johannes, et al., Zr-catalyzed kinetic resolution of allylic ethers and Mo-catalyzed chromene formation in synthesis. Enantioselective total synthesis of the antihypertensive agent (S,R,R,R)-nebivolol, J. Am. Chem. Soc., 1998, 120 (33):8340-8347.
Yang, et al., Synthesis and resolution research of (R)- and (S)-6-fluorochroman-2-carboxylic acids, Chinese Journal of Organic Chemistry, 2005, 25(2):201-203.

* cited by examiner

*Primary Examiner* — Bernard Dentz
(74) *Attorney, Agent, or Firm* — Lucas & Mercanti, LLP

(57) ABSTRACT

The present invention relates to a process for preparing nebivolol and, more particularly, to a process for preparing d-nebivolol and its enantiomer l-nebivolol or acid addition salts thereof starting from commercially available or easily obtainable 2,2-dimethyl-1,3 dioxolane-4-carbaldehyde and a vinyl Grignard reagent.

28 Claims, No Drawings

PROCESS FOR PREPARING NEBIVOLOL

This application is a 371 of PCT/EP2007/010185 filed on Nov. 23, 2007, which claims the benefit of European Patent Application No. 06124837.3 filed on Nov. 27, 2006, the contents of each of which are incorporated herein by reference.

The present invention relates to a process for preparing [2S[2R[R[R]]]]α,α'-[imino-bis (methylene)]bis[6-fluoro-chroman-2-methanol] (hereinafter also referred to as d-NBV) of formula (IA)

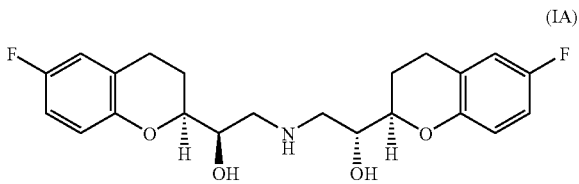

and its [2R[2S[S[S]]]] enantiomer (hereinafter also referred to as l-NBV) of formula (IB)

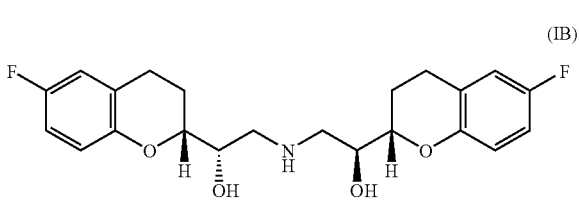

Nebivolol (hereinafter also referred to as NBV), a mixture of equal amounts of the two above enantiomers, is characterized by β-adrenergic blocking properties and is useful for the treatment of essential hypertension. Nebivolol has basic properties and may be converted into its pharmaceutically acceptable acid addition salt forms by treatment with appropriate acids. The hydrochloride acid addition salt is the marketed product.

It is well understood in the art that the synthesis of α,α'-[imino-bis(methylene)]bis[chroman-2-methanol] molecular structures is challenging for the skilled person, because of the 4 asymmetric carbon atoms producing a mixture of 16 stereoisomers (in case of asymmetrical substitution) or a mixture of 10 stereoisomers (in case of symmetrical substitution). As apparent from the presence of the topological symmetry in the structure of the α,α'-[imino-bis(methylene)]bis[6-fluoro-chroman-2-methanol], 10 stereoisomers can be generated.

The European patent application EP 145067 describes methods for the preparation of substituted α,α'-[imino-bis(methylene)]bis[chroman-2-methanol] including the 6,6' bis-fluoro derivatives, which comprises reducing chroman-2-carboxylic acid into the corresponding aldehyde and then transforming the aldehyde into the corresponding oxirane as a mixture of (R,S), (S,R), (RR) and (SS) stereoisomers. Oxirane stereoisomers, separated with column chromatography into racemic (R,S) and (S,R) oxirane and racemic (R,R) and (S,S) oxirane, represent the key intermediates of the process.

The European patent application EP 334429 describes the same synthetic process reported in EP 145067 and is particularly directed to the preparation of the (R,S,S,S) isomer (l-NBV). The existence of the 4 stereogenic centres moved the skilled person towards the exploration of stereoselective methods for preparing the l-NBV and the d-NBV. For example, Johannes C. W. et al. (J. Am. Chem. Soc., 120, 8340-8347, 1998) and Chandrasekhar S. et al. (Tetrahedron 56, 6339-6344, 2000) describe enantioselective total preparations of d-NBV; An-Guang Yu et al. (Synlett, 9, 1465-1467, 2005) illustrate a method for the construction of chiral chroman intermediates, and Yang Yun-Xu et al. (Chinese Journal of Organic Chemistry, 25(2), 201-203, 2005 and the Chinese patent application CN 1629154) show the synthesis and resolution of (R) and (S) 6-fluorochroman carboxylic acids intermediates useful for the synthesis of d-NBV and l-NBV.

Additional alternative total synthetic approaches for the preparation of NBV can be found in the following international patent applications: WO 2004/041805, WO 2006/016376 and WO 2006/025070.

We have now found an efficient alternative synthesis of l-NBV and d-NBV starting from inexpensive commercially available or easily obtainable starting materials.

It is therefore a first object of the present invention a process for preparing d-NBV of formula

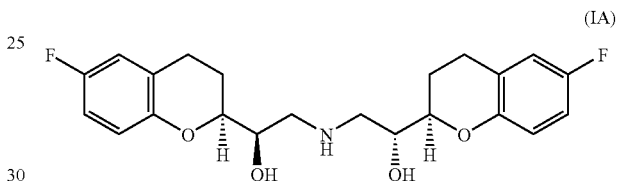

which comprises:

a) reacting 2,2-dimethyl-1,3 dioxolane-4-carbaldehyde of formula

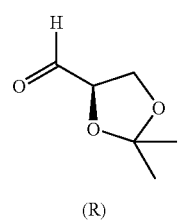

with a vinyl Grignard reagent, to obtain a compound of formula IIa in the form of diastereomeric mixture (S,R+R,R)

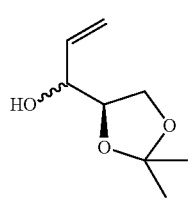

b) reacting the above compound of formula IIa with 2-bromo-4-fluorophenol to obtain a compound of formula IIIa in the form of diastereomeric mixture (S,R+R,R)

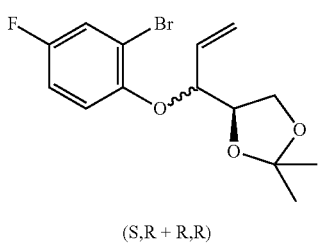

(S,R + R,R)

c) reacting the compound of the above formula IIIa with an organoborane compound of formula

IIIc wherein each Y is a siamyl group, an isopropyl-prenyl group, a cyclohexyl group, an isopinocampheyl group and a thexyl group;

or both Y taken together with the boron atom to which they are linked form a borabicyclo[3.3.1]non-9-yl group or a residue of formula:

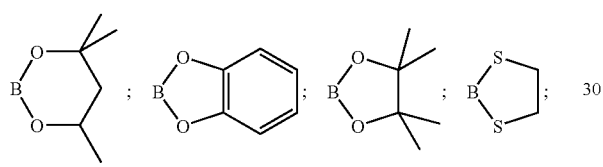

to obtain a compound of formula IVa in the form of diastereomeric mixture (S,R+R,R)

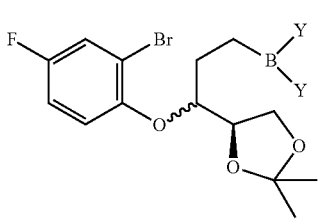

IVa (S,R + R,R)

wherein
Y is defined above;

d) cyclizing the above compound of formula IVa to obtain a compound of formula Va in the form of diastereomeric mixture (S,R+R,R)

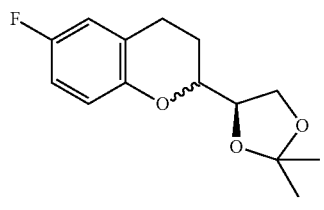

Va (S,R + R,R)

and, if desired, separating the compound of formula Va (S,R+R,R) into the single diastereomer Va (S,R) and the single diastereomer Va (R,R);

e) hydrolysing the diastereomeric mixture of formula Va (S,R+R,R) or, alternatively, hydrolysing separately the diastereomer Va (S,R) and the diastereomer Va (RR), to obtain the corresponding diastereomeric mixture of formula VIa (S,R+R,R)

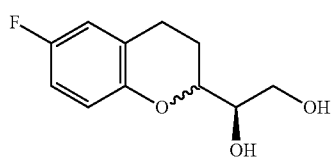

VIa (S,R + R,R)

or, independently, the diastereomer VIa (S,R)

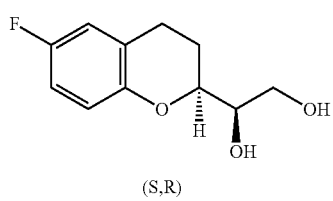

VIa (S,R)

and the diastereomer VIa (RR)

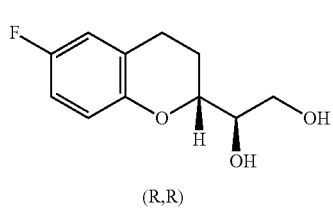

VIa (R,R)

f) reacting the diastereomeric mixture of formula VIa (S,R+R,R), or alternatively reacting separately the diastereomer VIa (S,R) and the diastereomer VIa (R,R) with a reactant able to introduce a good leaving group to obtain the corresponding diastereomeric mixture of formula VIIIa (S,R+R,R)

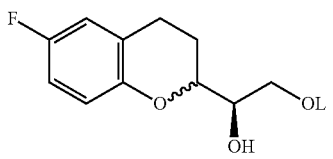

VIIa (S,R + R,R)

or, independently, the diastereomer VIIa (S,R)

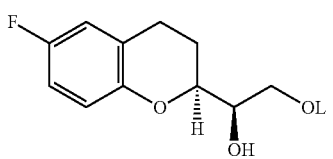

VIIa (S,R)

and the diastereomer VIIa (R,R)

![Structure VIIa (R,R): 6-fluorochroman with CH(OH)-CH2-OL substituent]

VIIa (R,R)

wherein

L is tosyl or mesyl;

g) reacting the diastereomeric mixture of formula VIIIa (S,R+R,R), or alternatively reacting separately the diastereomer VIIa (S,R) and the diastereomer VIIa (R,R) with a base to obtain the corresponding diastereomeric mixture of formula VIIIa (S,R+R,R)

![Structure VIIIa (S,R + R,R): 6-fluorochroman with epoxide]

VIIIa (S,R + R,R)

or, independently, the diastereomer VIIa (S,R)

![Structure VIIIa (S,R)]

VIIIa (S,R)

and the diastereomer VIIIa (R,R)

![Structure VIIIa (R,R)]

VIIIa (R,R)

and separating, if the case, the diastereomeric mixture of formula VIIIa (S,R+R,R) into the single diastereomer VIIIa (S,R) and the single diastereomer VIIIa (R,R);

h) reacting separately the compound of formula VIIIa (S,R) or the compound of formula VIIIa (R,R) with a protected H$_2$N—P amine wherein P is a nitrogen protecting group, to obtain a compound of formula IXa (S,R) or a compound of formula IXa (R,R)

![Structure IXa (S,R)]

IXa (S,R)

![Structure IXa (R,R)]

IXa (R,R)

i) reacting the compound of formula IXa (S,R) or the compound of formula IXa (R,R) with a compound of formula VIIIa (R,R) or a compound VIIIa (S,R) respectively, to obtain a compound of formula Xa (S,R,R,R) or a compound Xa (R,R,R,S), being the compound of formula Xa (S,R,R,R) the same stereoisomer of the compound Xa (R,R,R,S), because of the presence in the structure of compound Xa of an axis of symmetry which contains the nitrogen atom ![Structure Xa (S,R,R,R)]

Xa (S,R,R,R)

i.e.

![Structure Xa (R,R,R,S)]

Xa (R,R,R,S)

j) deprotecting the compound of formula Xa to give d-NBV of the above formula IA;

k) and, if desired, salifying the compound of formula IA.

It is a second object of the present invention a process for preparing l-NBV of formula ![Structure IB]

(IB)

which comprises l) reacting 2,2-dimethyl-1,3 dioxolane-4-carbaldehyde of formula

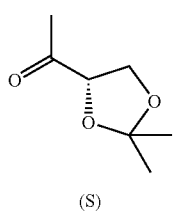

Ib (S)

with a vinyl Grignard reagent to obtain a compound of formula IIb in the form of diastereomeric mixture (R,S+S,S)

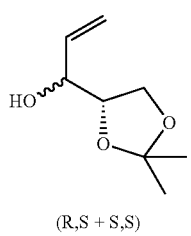

IIb (R,S + S,S)

m) reacting the above compound of formula IIb with 2-bromo-4-fluorophenol to give a compound of formula IIIb in the form of diastereomeric mixture (R,S+S,S)

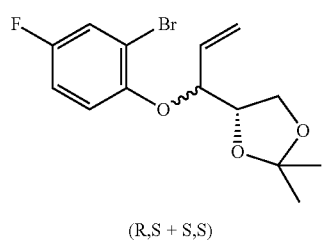

IIIb (R,S + S,S)

n) reacting the compound of the above formula IIIb with an organoborane compound of formula

IIIc wherein Y is defined above; to obtain a compound of formula IVb in the form of diastereomeric mixture (R,S+S,S)

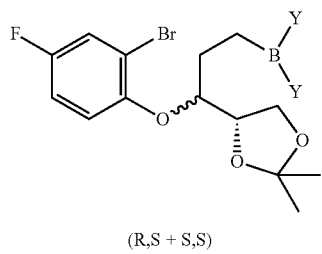

IVb (R,S + S,S)

wherein Y is defined above;
o) cyclizing the above compound of formula IVb to obtain a compound of formula Vb in the form of diastereomeric mixture (R,S+S,S)

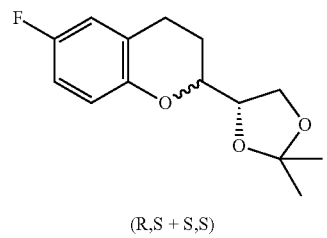

Vb (R,S + S,S)

and, if desired, separating the compound of formula Vb (R,S+S,S) into the single diastereomer Vb (R,S) and the single diastereomer Vb (S,S);

p) hydrolysing the diastereomeric mixture of formula Vb (R,S+S,S) or, alternatively, hydrolysing separately the diastereomer Vb (R,S), and the diastereomer Vb (S,S) to obtain the corresponding diastereomeric mixture of formula VIb (R,S+S,S)

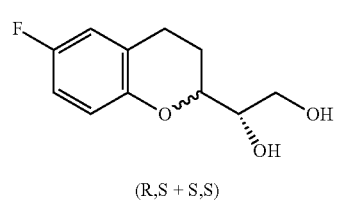

VIb (R,S + S,S)

or, independently, the diastereomer VIb (R,S)

VIb (R,S)

and the diastereomer VIb (S,S)

VIb (S,S)

q) reacting the diastereomeric mixture of formula VIb (R,S+S,S) or, alternatively, reacting separately the diastereomer VIb (R,S) and the diastereomer VIb (S,S) with a reactant able to introduce a good leaving group, to obtain the corresponding diastereomeric mixture of formula VIIb (R,S+S,S)

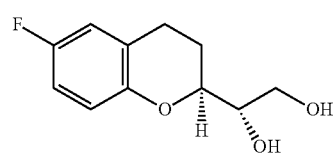

VIIb (R,S + S,S)

or, independently, the diastereomer VIIb (R,S)

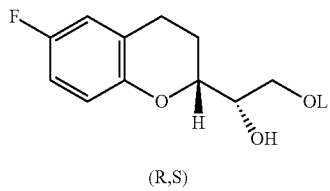

(R,S)

and the diastereomer VIIb (S,S)

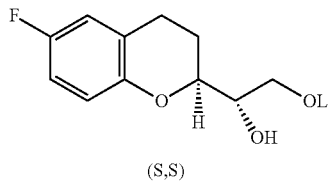

(S,S)

wherein
L is defined above
r) reacting the diastereomeric mixture of formula VIIb (R,S+S,S), or, alternatively, reacting separately the diastereomer VIIb (R,S) and the diastereomer VIIb (S,S) with a base to give the corresponding diastereomeric mixture of formula VIIIb (R,S+S,S)

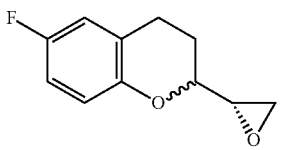

(R,S + S,S)

or, independently, the diastereomer VIIb (R,S)

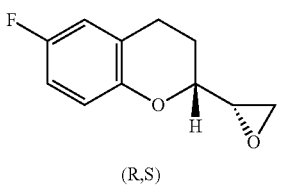

(R,S)

and the diastereomer VIIb (S,S)

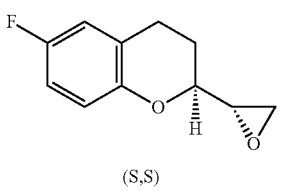

(S,S)

and separating, if the case, the diastereomeric mixture of formula VIIIb (R,S+S,S) into the single diasteromer VIIIb (R,S) and the single diasteromer VIIIb (S,S);
s) reacting separately the compound of formula VIIIb (R,S) or the compound of formula VIIIb (S,S) with a protected H₂N—P amine wherein P is a nitrogen protecting group to give a compound of formula IXb (R,S) or a compound of formula IXb (S,S)

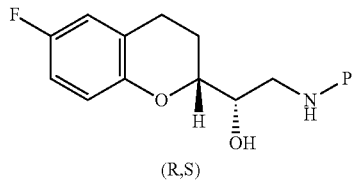

(R,S)

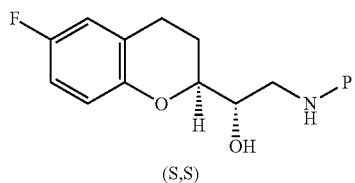

(S,S)

t) reacting the compound of formula IXb (R,S) or the compound of formula IXb (S,S) with a compound of formula VIIIb (S,S) or a compound VIIIb (R,S) respectively, to obtain a compound of formula Xb (R,S,S,S) or a compound Xb (S,S,S,R), being the compound of formula Xb (R,S,S,S) the same stereoisomer of the compound Xb (S,S,S,R), because of the presence in the structure of compound Xb of an axis of symmetry which contains the nitrogen atom (R,S,S,S)

(S,S,S,R)

u) deprotecting the compound of formula Xb to give l-NBV of the above formula IB;
v) and, if desired, salifying the compound of formula IB.

It is another object of the present invention a process for preparing d-NBV of formula IA which comprises reaction steps from a) to d) to give a compound of formula Va in the form of diastereoisomeric mixture (S,R+R,R) and optionally separating said compound of formula Va (S,R+R,R) into the single diastereomer Va (S,R) and the single diastereomer Va (R,R).

It is another object of the present invention a process for preparing l-NBV of formula IB which comprises reaction steps l) to o) to give a compound of formula Vb in the form of diastereoisomeric mixture (R,S+S,S) and optionally separating said compound of formula Vb (R,S+S,S) into the single diastereomer Vb (R,S) and the single diastereomer Vb (S,S). Alternatively, the compounds of formula Va and Vb in the form of diastereoisomeric mixture or single diastereoisomer, key intermediates in the synthesis of d-NBV and l-NBV according to the invention, may be obtained via an intermolecular Heck reaction between a compound of formula IIa or IIb and 2-bromo-4-fluorophenol or a derivative thereof followed by reduction to chroman nucleus.

It is therefore another object of the present invention a process for preparing d-NBV of formula

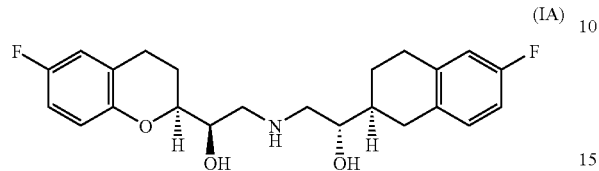
(IA)

which comprises:
a) reacting 2,2-dimethyl-1,3 dioxolane-4-carbaldehyde of formula

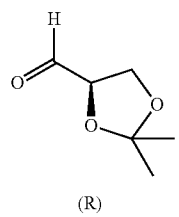
Ia
(R)

with a vinyl Grignard reagent, to obtain a compound of formula IIa in the form of diastereoisomeric mixture (S,R+R,R)

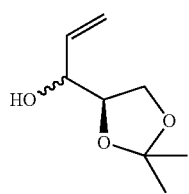
IIa
(S,R + R,R)

w) reacting the above compound of formula IIa with 2-bromo-4-fluorophenol or 2-bromo-4-fluorophenyl acetate by means of a palladium catalysed C—C coupling reaction, to obtain a compound of formula XIa in the form of diastereoisomeric mixture (S,R+R,R)

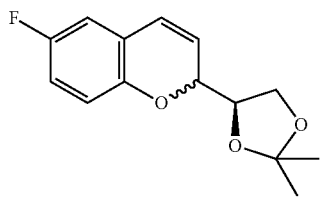
XIa
(S,R + R,R)

x) reducing the above compound of formula XIa to obtain a compound of formula Va in the form of diastereoisomeric mixture (S,R+R,R) and, if desired, separating the compound of formula Va (S,R+R,R) into the single diastereomer Va (S,R) and the single diastereomer Va (R,R).

It is another object of the present invention a process for preparing l-NBV of formula

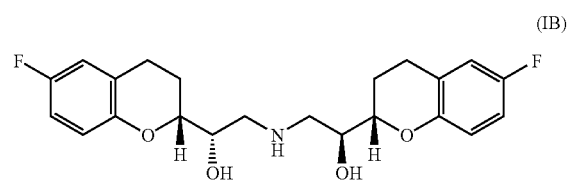
(IB)

which comprises:
l) reacting 2,2-dimethyl-1,3 dioxolane-4-carbaldehyde of formula

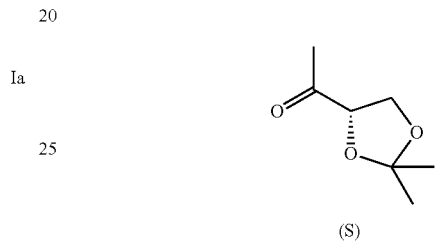
Ib
(S)

with a vinyl Grignard reagent to obtain a compound of formula IIb in the form of diastereoisomeric mixture (R,S+S,S)

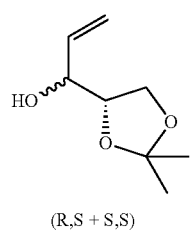
IIb
(R,S + S,S)

y) reacting the above compound of formula IIb with 2-bromo-4-fluorophenol or 2-bromo-4-fluorophenyl acetate by means of a palladium catalysed C-C coupling reaction to obtain a compound of formula XIb in the form of diastereoisomeric mixture (R,S+S,S)

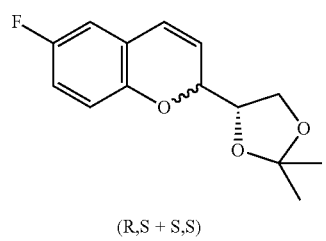
XIb
(R,S + S,S)

z) reducing the above compound of formula XIb to obtain a compound of formula Vb in the form of diastereoisomeric mixture (R,S+S,S) and, if desired, separating the compound of formula Vb (R,S+S,S) into the single diastereomer Vb (R,S) and the single diastereomer Vb (S,S).

It is evident to the skilled person that the intermediates XIa and XIb themselves may be subjected to reaction steps from e to k or from l to v, respectively, in place of intermediates Va and Vb in order to obtain the end products in accordance with the invention. Preferably, reduction from chromene to chroman nucleus may be carried out in final steps j/u by a hydrogenating reaction which allows a simultaneous deprotection/reduction of the so obtained compound [2S,αR,2'R,α'R]-α-α'-[[(phenylmethyl)imino]bismethylene]bis[6-fluoro-2H-1-benzopyran-2-methanol] or [2R,αS,2'S,α'S]-α-α'-[[(phenylmethyl)imino]bismethylene]bis[6-fluoro-2H-1-benzopyran-2-methanol] to give l-NBV or d-NBV.

As used herein, the symbols R and S show the absolute configuration at the asymmetric carbon atoms; a solid triangle represents a bond in the up configuration; a dashed triangle represents a bond in the down configuration; a wavy line denotes that the bond may be either in the up or in the down configuration and the asterisk means that the adjacent carbon atom is an asymmetric carbon atom.

The term "racemic mixture" refers to a compound in the form of a mixture of stereoisomers which are enantiomers. The term "diastereomeric mixture" refers to a compound in the form of a mixture of stereoisomers which are not enantiomers.

The abbreviation "Ph" as used herein represents the phenyl group. The abbreviation "Bn" as used herein represents the benzyl group. The abbreviation "Ts" as used herein represents the tosyl group.

Steps a/l:
the reaction of a compound of formula Ia or Ib to give a compound of formula IIa or IIb is carried out by adding a vinyl Grignard reagent such as vinyl magnesium bromide or vinyl magnesium chloride at a temperature ranging between −20° C. and 25° C. in the presence of organic solvent.

Preferred organic solvents are ethers or aprotic solvents such as toluene.

Preferably, a vinyl Grignard reagent is added dropwise in 5 min to 6 h to a solution of the compound of formula Ia or Ib at around 0° C.

Alternatively, a solution of the compound of formula Ia or Ib is added dropwise in 5 min to 6 h to a vinyl magnesium bromide or chloride solution at around 0° C.

The reaction may be then left to stir at temperatures ranging between −20° C. and 25° C. for 1-24 h before standard work-up.

Steps b/m:
the reaction of a compound of formula IIa or IIb with 2-bromo-4-fluoro-phenol to give a compound of formula IIIa or IIIb is carried out under Mitsunobu conditions in the presence of a phosphine such as triphenylphosphine (TPP) or tri-n-butylphosphine (TBP) and an aza compound such as diisopropylazadicarboxylate (DIAD), diethylazadicarboxilate (DEAD) and 1,1'-(azodicarbonyl)-dipiperidine (ADDP).

Generally, the reaction is carried out in ether solvents such as THF or aprotic solvents such as toluene at a temperature ranging between −20° C. and 50° C.

In a preferred embodiment of the invention, DIAD is added dropwise to a THF solution containing a compound of formula IIa or IIb, 2-bromo-4-fluoro-phenol and TPP at around 0° C. At addition completed, the reaction is worked-up immediately or, preferably, it is stirred at a temperature ranging between 0° C. and 80° C. for 1-24 h to give a compound of formula IIIa or IIIb.

Steps c/n:
the reaction of a compound of formula IIIa or IIIb to give a compound of formula IVa or IVb is carried out by reacting with an organoborane compound of formula

wherein Y is defined above;

Reagents such as 9-BBN (9-borabicyclo[3.3.1]nonane), disiamylborane, di(isopropyl-prenyl)borane, dicyclohexylborane, diisopinocampheylborane and thexylborane or dialkoxyboranes or heterocyclic boranes such as 4,4,6-trimethyl-1,3,2-dioxaborinane, 1,3,2-benzodioxaborole (catecholborane), pinacolborane and 1,3,2-dithiaborolane, are used as hydroborating agent.

Preferred, hydroborating agent is 9-BBN.

Generally, the reaction is carried out in ether solvents such as THF or aprotic solvents such as toluene at a temperature ranging between −20° C. and 100° C.

According to the invention the hydroboration reaction can also be carried out by using, as hydroborating agent, stoichiometric amounts of alkoxyboranes such as catecholborane with catalytic amounts of boranes such as dicyclohexylborane at temperatures ranging between −20° C. to 50° C.

Alternatively, the hydroboration is performed under rhodium catalyzed conditions for example by reacting a compound of formula IIIa or IIIb with stoichiometric catecholborane or pinacolborane in the presence of Wilkinson catalyst, [Rh(COD)Cl]₂.

Steps d/o:
the cyclization of a compound of formula IVa or IVb to give a compound of formula Va or Vb is carried out under B-alkyl Suzuki conditions.

Generally, the reaction is carried out under basic conditions, in the presence of a palladium catalyst.

In a preferred embodiment of the invention, a solution of a compound of formula IVa or IVb, prepared in situ as described above, is reacted with 1-3 equivalents of base, in the presence of 0.01 to 10 mol % of ligandless palladium or a palladium complex and optionally in the presence of additives such as silver oxide or phase transfer catalysts such as tetrabutyl ammonium chloride and tetrabutyl ammonium bromide; the reaction takes place in the presence of an organic solvent or water at a temperature ranging between 18° C. to 200° C. Basic conditions are obtained by using a suitable amount of a base, preferably, a mineral base such as potassium carbonate, sodium carbonate, cesium carbonate, sodium hydrogen carbonate, potassium hydrogen carbonate lithium hydroxide, sodium hydroxide, potassium hydroxide, cesium hydroxide, tallium hydroxide, sodium acetate, potassium acetate, sodium phosphate and potassium phosphate or amines such as triethylamine and the like.

Ligandless palladium such as palladium acetate, palladium chloride or palladium(0) on carbon are used optionally in the presence of 0.01 to 1 mol % of a phase transfer compound such as tetrabutyl ammonium chloride or tetrabutyl ammonium bromide.

The palladium complex can be generated in situ, typically from a palladium source such as palladium acetate or palladium chloride, and a ligand such as triphenylphosphine, 1,1-bis-(di-t-butylphosphino)-ferrocene, o-tritolylphosphine, m-tritolylphosphine, tricyclohexylphosphine, diphenylphosphinoferrocene, 2,4,6 trioxy 1,3,5,7 tetramethyl-8-phosphaadamantane, dibenzylideneacetone (dba), tri-t-butylphosphine and tri-n-butylphosphine.

The palladium complex can be directly used as preformed catalyst in the form of Pd(0) and Pd(II) complexes such as palladium tetrakis, PdCl$_2$(PPh$_3$)$_2$, PdCl$_2$(dppf), di-t-bpf-PdCl$_2$, Pd$_2$dba$_3$, Pd(t-Bu$_3$P)$_2$ and the like.

Protic and aprotic solvents optionally in admixture are used in the C—C coupling reaction. Preferably, DMF, DMA, DMSO, methanol, ethanol, i-propanol, water, toluene, acetonitrile, THF and the like, are used.

Product isolation and optional separation of single diastereoisomers are accomplished in accordance with known methods. Preferably said diastereoisomer separation is performed via chromatography.

Steps e/p:

the deprotection of a compound of formula Va or Vb to give a compound of formula VIa or VIb is carried out under acidic conditions.

Suitable acids are organic or mineral acids. An acidic resin may also be used for the purpose of the present invention.

Generally, the deprotection is carried out in the presence of an organic solvent; preferably, protic or aprotic solvents are used.

A preferred embodiment of the invention provide dissolving a compound of formula Va or Vb in acetic acid and demi water and stirring the obtained mixture at a temperature ranging between 25° C. to reflux for 1-24 h.

Product isolation and optional separation of single diastereoisomers are accomplished in accordance with known methods. Preferably said diastereoisomer separation is performed via chromatography or crystallization.

Steps f/q:

the reaction of a compound of formula VIa or VIb with a reactant able to introduce a good leaving group to give a compound of formula VIIIa or VIIb is carried out according to known techniques.

Suitable reactants able to introduce a good leaving group are mesyl chloride or tosyl chloride.

Generally, the reaction is carried out in the presence of a tosylating agent such as tosylchloride and a mineral or organic base in protic or aprotic solvents optionally in admixtures.

Suitable bases are mineral bases, such as potassium carbonate, sodium carbonate, sodium hydroxide, potassium hydroxide, or organic bases such as pyridine, triethylamine, DIPEA and DMAP.

Suitable solvent are protic solvents, such as alcohols, water or organic aprotic solvents such as dichloromethane, chloroform, DCE, toluene, pyridine, DMF, DMA, DMSO and acetonitrile. Mixtures of solvents may be also used as suitable reaction media (e.g. water and toluene under phase transfer conditions).

The skilled person will realize that a compound of formula VIa or VIb may be subjected to alternative reactions able to introduce a good leaving group without departing from the spirit of the invention.

Steps g/r:

the reaction of a compound of formula VIIIa or VIIb to give a compound of formula VIIIa or VIIIb is carried out by reacting with a base according to known techniques.

A practical embodiment of the invention foresees reacting a compound of formula VIIIa or VIIb with a mineral or organic base such as potassium carbonate, sodium carbonate, potassium hydrogen carbonate, sodium hydrogen carbonate, potassium hydroxide, sodium hydroxide, triethylamine, pyridine and DIPEA in the presence of protic or aprotic solvents for around 1 to 24 h at a temperature comprised between 0° C. and 130° C.

A preferred embodiment of the invention provides reacting a compound of formula VIIIa or VIIb with potassium carbonate in mixtures of dichloromethane and methanol at 25° C. for 1 to 20 h.

Alternatively, the tosylation reaction and the formation of the epoxide ring can also be performed in a one pot-procedure.

For example, a compound of formula VIa or VIb may be reacted with tosyl chloride, with a base such as sodium hydroxide in water solution, in the presence of a solvent such as dichloromethane or toluene and a phase transfer agent such as TBAC or TBAB or TEBA at 18-120° C. to give directly a compound of formula VIIIa or VIIIb.

Product isolation and optional separation of single diastereoisomers are accomplished in accordance with known methods. Preferably said diastereoisomer separation is performed via chromatography.

Steps h/s:

the reaction of a compound of formula VIIIa (S,R) or VIIIa (R,R) to give a compound of formula IXa (S,R) or IXa (R,R) as well as the reaction of a compound of formula VIIb (R,S) or VIIIb (S,S) to give a compound of formula IXb (R,S) or IXb (S,S) are carried out by reacting with a protected H$_2$N—P amine wherein P is a nitrogen protecting group according to known techniques.

Suitable nitrogen protecting groups are benzyl, p-methoxy benzyl, trityl, cbz groups which are all readily cleaved via hydrogenation. Preferred protected H$_2$N—P amine is benzyl amine. Generally, the reaction is performed in the presence of an organic solvent. Preferred solvents are protic or aprotic solvents.

A preferred embodiment of the invention provides reacting a compound of formula VIIIa (S,R) or VIIIa (R,R) or VIIIb (R,S) or VIIIb (S,S) with benzyl amine in an alcoholic solvent such as methanol, ethanol, 2-propanol and the like at a temperature comprised between 18° C. and reflux and separating the obtained products IXa (S,R) or IXa (R,R) or IXb (R,S) or IXb (S,S) by crystallization.

Steps i/t:

the reaction of a compound of formula IXa (S,R) or IXa (R,R) with a compound of formula VIIIa (R,R) or VIIIa (S,R) respectively, to give a compound of formula Xa (S,R,R,R) or Xa (R,R,R,S) as well as the reaction of a compound of formula IXb (R,S) or IXb (S,S) with a compound of formula VIIIb (S,S) or VIIIb (R,S) respectively, to give a compound of formula Xb (R,S,S,S) or Xb (S,S,S,R), are carried out in the presence of an organic solvent. Preferred organic solvents are alcohols and, preferably, ethanol is used.

Reaction temperature is generally comprised between 18° C. and reflux.

In a preferred embodiment of the invention compounds of formula Xa (S,R,R,R), Xa (R,R,R,S), Xb (R,S,S,S) and Xb (S,S,S,R) are obtained by stirring respective starting materials in ethanol at reflux temperature for 1 to 24 h. The products are separated by crystallization.

Steps j/u:

deprotection of a compound of formula Xa to give d-NBV of formula IA as well as deprotection of a compound of formula Xb to give l-NBV of formula IB are carried out according to known techniques.

In a preferred embodiment of the invention N-benzyl derivatives of formula Xa or Xb are deprotected under hydrogenation conditions. For example, deprotection is carried out by using Pd/C as catalyst in the presence of an organic solvent such as alcohols. The reaction may be carried out under neutral, acidic or basic conditions. Hydrogen may be also generated in situ by using a hydrogen source such as formic acid, ammonium formate, phosphoric acid, cyclohexene and cyclohexadiene, under catalytic hydrogen transfer reduction conditions.

Steps k/v:

if desired compounds of formula IA or IB are salified as salts of mineral or organic acids in accordance with known methods. In a preferred embodiment of the invention compounds of formula IA or IB are salified as hydrochloride salts in the presence of alcoholic solvents.

Steps w/v:

the reaction of a compound of formula IIa or IIb with 2-bromo-4-fluorophenol or 2-bromo-4-fluorophenyl acetate to give a compound of formula XIa or XIb is carried out by a one pot or, alternatively, a stepwise procedure.

In one embodiment of the invention, the procedure comprises a one pot Heck reaction and cyclization of a compound of formula IIa or IIb with 2-bromo-4-fluorophenyl acetate to give a compound of formula XIa or XIb.

Generally, the reaction is carried out in basic conditions, in the presence of a palladium catalyst under Heck C—C couplings in accordance with what is described in the above steps d/o.

In another embodiment of the invention, the compound of formula XIa or XIb is obtained via a stepwise procedure by reacting 2-bromo-4-fluorophenol or 2-bromo-4-fluorophenyl acetate with a compound of formula Ia or IIb to give a compound of formula XIIa or XIIb which is subjected to cyclization conditions in accordance with the following scheme The first step is performed under Heck reaction conditions as described above for the one pot procedure. In a preferred embodiment, the C—C coupling reaction between 2-bromo-4-fluorophenol and a compound of formula IIa or IIb is carried out in the presence of a palladium catalyst and a base in an admixture of an organic solvent and water at 50-90° C. to give a compound of formula XIIa or XIIb and, respectively, a compound of formula XIIIa or XIIIb.

Separation of the compound of formula XIIa or XIIb from the compound of formula XIIIa or XIIIb, and optional separation of single diastereoisomers are accomplished in accordance with known methods. Preferably said separations are both performed via chromatography. Cyclization step is performed under Lewis Acid mediated conditions. In a preferred embodiment of the invention a compound of formula XIIa or XIIb is reacted with zinc chloride at a temperature ranging between 25 to 150° C. in organic solvents such as toluene, xylene, dichloromethane, chloroform, dichloroethane, tetrahydrofuran, methyl-tetrahydrofuran and the like, to give a compound of formula XIa or XIb.

The reaction may be optionally carried out in the presence of additives such as lithium chloride.

Product isolation and optional separation of single diastereoisomers are accomplished in accordance with known methods. Preferably said diastereoisomer separation is performed via chromatography.

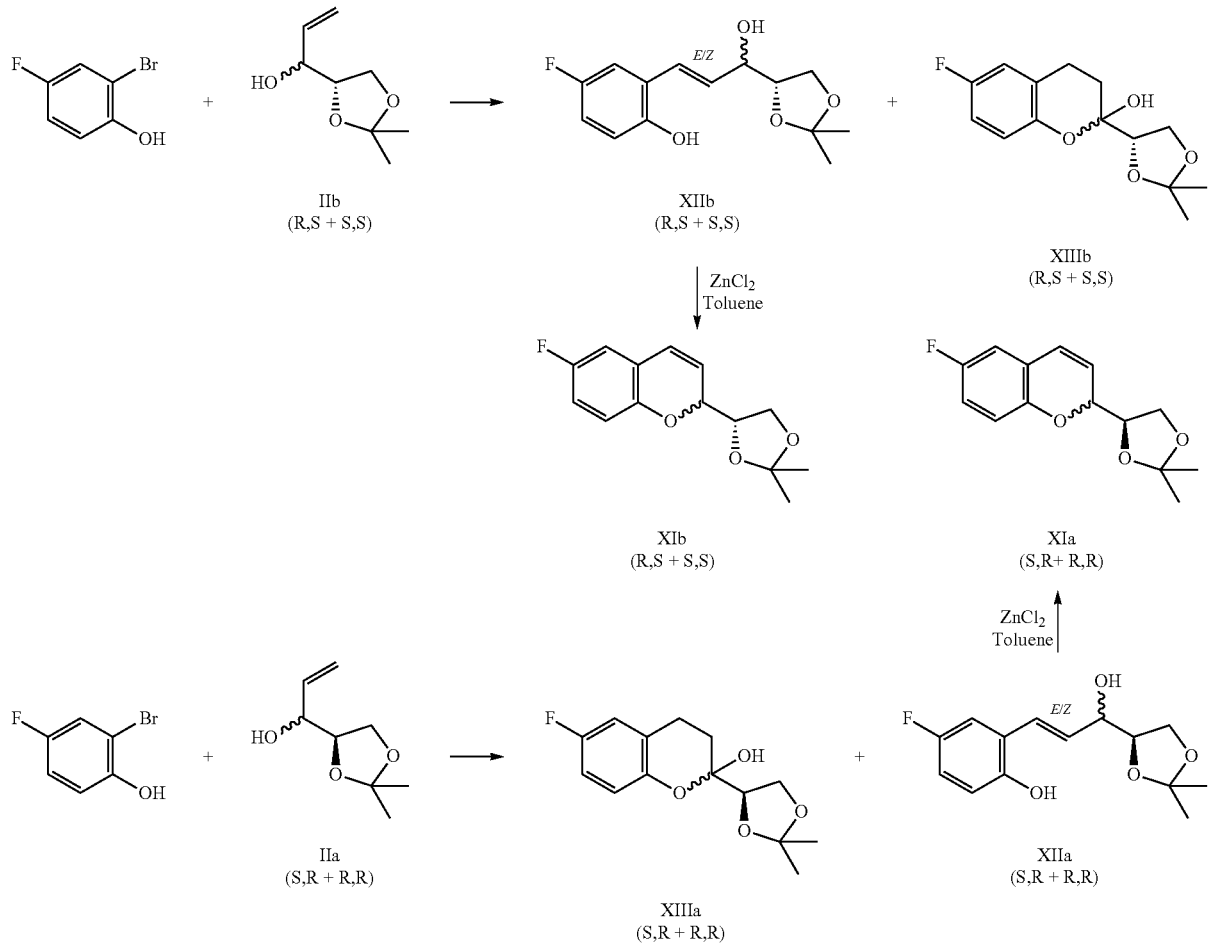

Steps x/z:

the reduction of a compound of formula XIa or XIb to give a compound of formula Va or Vb is carried out by known techniques.

Generally, an unsaturated compound of formula XIa or XIb is reduced under hydrogenation conditions to give correspondent saturated compound of formula Va or Vb.

For example, hydrogenation reaction is carried out in accordance with what is described in the above steps j/u.

Product isolation and optional separation of single diastereoisomers are accomplished in accordance with known methods. Preferably said diastereoisomer separation is performed via chromatography.

A further aspect of the present invention refers to a compound of formula:
(S)-4-(1-((R,S)-2-bromo-4-fluorophenoxy)-allyl)-2,2-dimethyl-1,3-dioxolane;
(R)-4-(1-((R,S)-2-bromo-4-fluorophenoxy)-allyl)-2,2-dimethyl-1,3-dioxolane;
(R)-2-(benzylamino)-1-((S)-6-fluoro-3,4-dihydro-2H-chromen-2-yl)ethanol;
(S)-4-(1-((R,S)-2-bromo-4-fluorophenoxy)-3-(borabicyclo[3.3.1]non-9-yl)-propyl)-2,2-dimethyl-1,3-dioxolane;
(R)-4-(1-((R,S)-2-bromo-4-fluorophenoxy)-3-(borabicyclo[3.3.1]non-9-yl)-propyl)-2,2-dimethyl-1,3-dioxolane;
(S,R)-4-fluoro-2-((E/Z)-3-hydroxy-3-((R)-2,2-dimethyl-1,3-dioxolan-4-yl)prop-1-enyl)phenol;
(S,R)-4-fluoro-2-((E/Z)-3-hydroxy-3-((S)-2,2-dimethyl-1,3-dioxolan-4-yl)prop-1-enyl)phenol;
(S,R)-6-fluoro-3,4-dihydro-2-((R)-2,2-dimethyl-1,3-dioxolan-4-yl)-2H-chromen-2-ol;
(S,R)-6-fluoro-3,4-dihydro-2-((S)-2,2-dimethyl-1,3-dioxolan-4-yl)-2H-chromen-2-ol;

as useful intermediates in the preparation of d-NBV and l-NBV.

A further aspect of the present invention refers to a compound of formula:
(±)[R*,S*,S*,S*]-α-α'-[iminobismethylene]bis[6-fluoro-3,4-dihydro-2H-1-benzopyran-2-methanol] formate;
[2S,αR,2'R,α'R]-α-α'-[iminobismethylene]bis[6-fluoro-3,4-dihydro-2H-1-benzopyran-2-methanol] formate;
[2R,αS,2'S,α'S]-α-α'-[iminobismethylene]bis[6-fluoro-3,4-dihydro-2H-1-benzopyran-2-methanol] formate;

as new salified forms of NBV useful in the preparation of a highly pure end-product.

A practical embodiment of the process object of the present invention comprises reacting a compound of formula Ia or Ib with a vinyl Grignard reagent at a temperature ranging between −20° C. and 25° C. in the presence of organic solvent; so obtained compounds of formula IIa or IIb are reacted with 2-bromo-4-fluoro-phenol under Mitsunobu conditions in the presence of a phosphine, an aza compound and an organic solvent to give a compound of formula IIIa or IIIb which is further reacted with an organoborane compound at a temperature ranging between −20° C. and 100° C. in the presence of an ether or an aprotic solvent; so obtained compounds of formula IVa or IVb are cyclized under basic conditions in the presence of a palladium catalyst and protic or aprotic solvents optionally in admixture to give a compound of formula Va or Vb in the form of diastereoisomeric mixture (S,R+R,R); said mixture is then separated into single diastereoisomer Va (S,R) and Va (R,R) or Vb (S,R) and Vb (R,R) by chromatography according to known methods; the compounds of formula Va (S,R) and Va (R,R) or Vb (S,R) and Vb (R,R) are hydrolyzed in acidic conditions to the correspondent diols of formula VIa (S,R) and VIa (R,R) or VIb (S,R) and VIb (R,R) which are subjected to a tosylation reaction and transformed in the epoxide derivatives of formula VIIIa (S,R) and VIIa (R,R) or VIIb (S,R) and VIIb (R,R) in the presence of a base; said compounds are then converted in d-NBV or l-NBV or salts thereof in accordance with known methods.

A preferred practical embodiment of the process object of the present invention comprises reacting a compound of formula Ia or Ib with vinyl magnesium bromide at a temperature ranging between −20° C. and 25° C. in the presence of ethers, preferably THF, or aprotic solvents; so obtained compounds of formula IIa or IIb are reacted with 2-bromo-4-fluoro-phenol under Mitsunobu conditions in the presence of TPP, DIAD in THF to give a compound of formula IIIa or IIIb which is further reacted with 9-BBN at a temperature ranging between −20° C. and 100° C. in THF or toluene; so obtained compounds of formula IVa or IVb are cyclized under basic conditions, preferably potassium carbonate, in the presence of a palladium catalyst and a protic or aprotic solvent, preferably DMF, optionally in admixture to give a compound of formula Va or Vb in the form of diastereoisomeric mixture (S,R+R,R); said mixture is then separated into single diastereoisomers Va (S,R) and Va (R,R) or Vb (S,R) and Vb (R,R) by chromatography according to known methods; the compounds of formula Va (S,R) and Va (R,R) or Vb (S,R) and Vb (R,R) are hydrolyzed in acidic conditions to the correspondent diols of formula VIa (S,R) and VIa (R,R) or VIb (S,R) and VIb (R,R) which are subjected to a tosylation reaction and transformed in the epoxide derivatives of formula VIIa (S,R) and VIIa (R,R) or VIIb (S,R) and VIIb (R,R) in the presence of a base; said compounds are then converted in d-NBV or l-NBV or salts thereof in accordance with known methods.

An alternative practical embodiment of the process object of the present invention comprises reacting a compound of formula Ia or Ib with a vinyl Grignard reagent at a temperature ranging between −20° C. and 25° C. in the presence of organic solvent; so obtained compounds of formula IIa or IIb are reacted with 2-bromo-4-fluoro-phenol or 2-bromo-4-fluorophenyl acetate under palladium catalysed mediated conditions by a one pot or a stepwise procedure, to give a compound of formula XIa or XIb which is further reduced under catalytic hydrogen transfer reduction conditions to give a compound of formula Va or Vb in the form of diastereoisomeric mixture (S,R+R,R); said mixture is then separated into single diastereoisomer Va (S,R) and Va (R,R) or Vb (S,R) and Vb (R,R) by chromatography according to known methods; the compounds of formula Va (S,R) and Va (R,R) or Vb (S,R) and Vb (R,R) are hydrolyzed in acidic conditions to the correspondent diols of formula VIa (S,R) and VIa (R,R) or VIb (S,R) and VIb (R,R) which are subjected to a tosylation reaction and transformed in the epoxide derivatives of formula VIIIa (S,R) and VIIa (R,R) or VIIb (S,R) and VIIb (R,R) in the presence of a base; said compounds are then converted in d-NBV or l-NBV or salts thereof in accordance with known methods.

It is to be understood that while the invention is described in conjunction of the preferred embodiments thereof, those skilled in the art are aware that other embodiments could be made without departing from the spirit of the invention.

For better illustrating the invention the following examples are now given.

EXAMPLE 1

Synthesis of (R)-4-(1-(2-bromo-4-fluorophenoxy) allyl)-2,2-dimethyl-1,3-dioxolane On a stirred solution of (R)-2,2-dimethyl-1,3-dioxolane-4-carbaldehyde (11.0 g, 0.063 mol, 75% assay, 94% ee) in THF (40 g) at 0° C. under nitrogen atmosphere, a vinyl magnesium bromide solution (1.0 M in THF, 88.7 ml, 0.0887 mol) was added over a period of 90 min. After 2 h stirring at 0° C., the temperature was raised to 10° C. and a saturated ammonium chloride solution (60 ml) was added dropwise in 30 min. The quenched reaction mixture at 20° C. was then diluted with ethyl acetate (100 ml) and demi water (50 ml) and the layers separated. The organic phase was further washed with demi water (50 ml). The organic phase was then dried over anhydrous magnesium sulfate, filtered and concentrated under reduced pressure to furnish 11.7 g of 1-((R)-2,2-dimethyl-1,3-dioxolan-4-yl)prop-2-en-1-ol as a light yellow oil. Spectroscopic data are conform to literature.

On a stirred solution composed by 2-bromo-4-fluoro-phenol (12.07 g, 0.063 mol) and triphenylphosphine (16.18 g, 0.063 mol) in THF (85 ml) under nitrogen at 18° C., 1-((R)-2,2-dimethyl-1,3-dioxolan-4-yl)-prop-2-en-1-ol (10.0 g, 0.054 mol) was added as a crude product. The reaction miture was then cooled to 0° C. and diisopropyl-aza-dicarboxylate (12.78 g, 0.063 mol) was added dropwise over a period of 30 min. At the end of the addition the temperature was raised gradually to 18° C. and the mixture left to stir for further 1 h. The crude reaction was then concentrated under reduced pressure and then MTBE (31 g) added. After 15 min agitation, the slurry was filtered and the panel washed with MTBE (2×10 g). The mother liquors were then concentrated in vacuo and heptane (23 g) added. After 30 min stirring, the slurry was filtered and the cake washed with heptane (11 g). The mother liquors were then concentrated in vacuo and purified by column chomatography on silica using a mixture heptan:ethyl acetate:triethylamine 9.5:0.5:0.01, as eluent. 14.28 g of (R)-4-(1-(2-bromo-4-fluorophenoxy)allyl)-2,2-dimethyl-1,3-dioxolane were isolated as a mixture of diastereoisomers (80% yield).

NMR: $\delta_H$(400 MHz; CDCl$_3$) 6.96-6.85 (6H, m), 5.97-5.82 (2H, m), 5.38-5.31 (4H, m), 4.70-4.65 (1H, m), 4.60-4.55 (1H, m), 4.43 (1H, dd, J 12, 6), 4.29 (1H, dd, J 12, 6), 4.19-4.07 (3H, m), 3.99-3.95 (1H, m), 1.47 (3H, s), 1.45 (3H, s), 1.40 (6H, s); m/z (EI) 330.0289 (M$^+$. C$_{14}$H$_{16}$BrFO$_3$ requires 330.0262).

EXAMPLE 2

Synthesis of 6-fluoro-3,4-dihydro-2-((R)-2,2-dimethyl-1,3-dioxolan-4-yl)-2H-chromene A solution of (R)-4-(1-(2-bromo-4-fluorophenoxy)-allyl)-2,2-dimethyl-1,3-dioxolane (1.00 g, 3.02 mmol) in THF (3 ml) was added over a period of 10 min to a stirred solution of 9-BBN (0.5 M in THF, 12.08 ml, 6.04 mmol) under nitrogen at 0° C. At the end of the addition the reaction mixture was heated to 25° C. and left to stir for 6 h.

A portion of the hydroboration solution (4 ml, 0.755 mmol) was added under nitrogen over a mixture composed by K$_2$CO$_3$ (0.337 g, 2.438 mmol), PdCl$_2$(dppf) (31.2 mg, 0.038 mmol) in DMF (3 ml). At the end of the addition, the mixture was heated to 65° C. and left to stir at this temperature for 17 h. The temperature was then raised to 75° C. and the reaction mixture stirred for further 5 h. After checking the reaction outcome, heptane (5 ml) and demi water (5 ml) were added under stirring and the phases separated. The aqueous phase was further extracted with heptane (2×5 ml) and the collected organic layers washed with demi water (10 ml). The separated organic phase was dried over anhydrous magnesium sulfate and then concentrated in vacuo to give the crude residue as a yellow oil. Purification by column chomatography on silica, using as eluent heptane:ethyl acetate:triethylamine in the ratio 9:1:0.01, furnished 110 mg of 6-fluoro-3,4-dihydro-2-((R)-2,2-dimethyl-1,3-dioxolan-4-yl)-2H-chromene as a mixture of diastereoisomers (58% yield).

NMR Diast. RR: $\delta_H$(400 MHz; CDCl$_3$) 6.81-6.72 (3H, m, Ar), 4.32-4.28 (1H, m), 4.10 (1H, dd, J 7, 7), 4.02 (1H, dddd, J 11, 6, 2), 3.91 (1H, dd, J 7, 7), 2.91-2.72 (2H, m), 1.96-1.74 (2H, m), 1.46 (3H, s), 1.41 3H, s);

NMR Diast. SR: $\delta$H(400 MHz; CDCl3) 6.81-6.70 (3H, m, Ar), 4.19 (1H, dd, J 8, 6), 4.14-4.10 (1H, m), 4.06 (1H, dd, J 8, 5), 3.88 (1H, ddd, J 10, 7, 2.3), 2.88-2.72 (2H, m), 2.26-2.18 (1H, m), 1.83-1.73 (1H, m), 1.45 (3H, s), 1.39 (3H, s); m/z (EI) 252.1139 (M$^+$. C$_{14}$H$_{17}$FO$_3$ requires 252.1157).

EXAMPLE 3

Synthesis of 6-fluoro-3,4-dihydro-2-((R)-2,2-dimethyl-1,3-dioxolan-4-yl)-2H-chromene A solution of (R)-4-(1-(2-bromo-4-fluorophenoxy)allyl)-2,2-dimethyl-1,3-dioxolane (3.8 g, 11.47 mmol) in THF (2 ml) was added over a period of 1 h to a stirred solution of 9-BBN (0.5 M in THF, 25.2 ml, 12.6 mmol) under nitrogen at 25° C. At the end of the addition the reaction mixture was stirred at 25° C. for 23 h.

A portion of the hydroboration solution (16 ml, 5.74 mmol) was added under nitrogen over a mixture composed by K$_2$CO$_3$ (0.793 g, 5.74 mmol), 2,4,6 trioxy 1,3,5,7 tetramethyl-8-phosphaadamantane (94.8 mg, 0.324 mmol), palladium acetate (64.4 mg, 0.287 mmol) in demi water (7 ml). At the end of the addition, the mixture was heated to 65° C. and left to stir at this temperature for 18 h. After checking the reaction outcome, heptane (20 ml) and demi water (20 ml) were added under stirring and the phases separated. The aqueous phase was further extracted with heptane (2×10 ml) and the collected organic layers washed with demi water (2×10 ml). The separated organic layer was dried over anhydrous magnesium sulfate and then concentrated in vacuo to give the crude residue as a yellow oil. Purification by column chomatography on silica, using as eluent heptane:ethyl acetate in the ratio 9.5:0.5, furnished 460 mg of 6-fluoro-3,4-dihydro-2-((R)-2,2-dimethyl-1,3-dioxolan-4-yl)-2H-chromene as a mixture of diastereoisomers (32% yield).

NMR Diast. RR: $\delta_H$(400 MHz; CDCl$_3$) 6.81-6.72 (3H, m, Ar), 4.32-4.28 (1H, m), 4.10 (1H, dd, J 7, 7), 4.02 (1H, dddd, J 11, 6, 2), 3.91 (1H, dd, J 7, 7), 2.91-2.72 (2H, m), 1.96-1.74 (2H, m), 1.46 (3H, s), 1.41 3H, s);

NMR Diast. SR: $\delta_H$(400 MHz; CDCl$_3$) 6.81-6.70 (3H, m, Ar), 4.19 (1H, dd, J 8, 6), 4.14-4.10 (1H, m), 4.06 (1H, dd, J 8, 5), 3.88 (1H, ddd, J 10, 7, 2.3), 2.88-2.72 (2H, m), 2.26-2.18 (1H, m), 1.83-1.73 (1H, m), 1.45 (3H, s), 1.39 (3H, s); m/z (EI) 252.1139 (M$^+$. C$_{14}$H$_{17}$FO$_3$ requires 252.1157).

EXAMPLE 4

Synthesis of (R)-1-((R)-6-fluoro-3,4-dihydro-2H-chromen-2-yl)ethane-1,2-diol

Diastereoisomeric mixture obtained in Example 3 was separated into the single diastereoisomers in accordance to known methods.

(R)-6-fluoro-3,4-dihydro-2-((R)-2,2-dimethyl-1,3-dioxolan-4-yl)-2H-chromene (2.92 g, 11.6 mmol) was dissolved in acetic acid (24 ml) and demi water (9 ml). The reaction mixture was stirred vigorously and heated to 65° C. After 3 h at 65° C. the reaction mixture was cooled to 25° C. The solution was then concentrated in vacuo to obtain a vetrous oil. Chromatographic separation on silica of the crude, using a mixture of heptane:ethyl acetate 1:1 as eluent, furnished 0.64 g of (R)-1-((R)-6-fluoro-3,4-dihydro-2H-chromen-2-yl) ethane-1,2-diol as a white solid (26% yield).

NMR: $\delta_H$(400 MHz; CDCl$_3$) 6.82-6.73 (3H, m), 4.10-4.03 (1H, m), 3.89-3.75 (3H, m), 2.93-2.74 (2H, m), 2.65 (1H, b), 2.10 (1H, b), 2.04-1.90 (2H, m). Chiral HPLC: ee 94%.

EXAMPLE 5

Synthesis of (R)-1-((S)-6-fluoro-3,4-dihydro-2H-chromen-2-yl)ethane-1,2-diol

Diastereoisomeric mixture obtained in Example 3 was separated into the single diastereoisomers in accordance to known methods.

(S)-6-fluoro-3,4-dihydro-2-((R)-2,2-dimethyl-1,3-dioxolan-4-yl)-2H-chromene (1.10 g, 4.4 mmol) was dissolved in acetic acid (9 ml) and demi water (3 ml). The reaction mixture was stirred vigorously and heated to 65° C. After 2.5 h at 60° C. the reaction mixture was cooled to 25° C. The solution was then concentrated in vacuo to obtain a vetrous oil. Chromatographic separation on silica of the crude, using a mixture of heptane:ethyl acetate 1:1 as eluent, furnished 0.40 g of (R)-1-((S)-6-fluoro-3,4-dihydro-2H-chromen-2-yl)ethane-1,2-diol as a white solid (43% yield).

NMR: $\delta_H$(400 MHz; CDCl$_3$) 6.83-6.69 (3H, m, Ar), 4.05-3.98 (1H, m), 3.90-3.80 (3H, m), 2.91-2.74 (2H, m), 2.18-2.11 (1H, m), 1.91-1.81 (1H, m). Chiral HPLC: ee 94%.

EXAMPLE 6

Synthesis of (R)-6-fluoro-3,4-dihydro-2-((R)-oxiran-2-yl)-2H-chromene (R)-1-((R)-6-fluoro-3,4-dihydro-2H-chromen-2-yl) ethane-1,2-diol (0.27 g, 1.27 mmol) was dissolved in dichloromethane (7 ml) under nitrogen atmosphere and pyridine (100 µl) added under stirring. The reaction mixture was then cooled to 0° C. and tosyl chloride (0.24 g, 1.27 mmol) in dichloromethane (3 ml) was added over a period of 2 h. The temperature was then raised to 20° C. and left under agitation for 15 h. The reaction was quenched with water (10 ml) and further diluted with dichloromethane (10 ml). The aqueous layer was separated and further extracted with dichloromethane (15 ml). The collected organic layers are dried over magnesium sulfate, filtered and concentrated in vacuo to furnish a colourless oil. Said oil was dissolved in methanol (3 ml) and dichloromethane (6 ml) under stirring in nitrogen atmosphere and potassium carbonate (0.32 g, 2.35 mmol) added. The reaction mixture was left to stir for 15 h at 25° C. The reaction was then diluted with water (10 ml) and dichloromethane (10 ml). The separated aqueous layer was then extracted with dichloromethane (20 ml). The collected organic layers were dried over magnesium sulfate and concentrated in vacuo to furnish crude (R)-6-fluoro-3,4-dihydro-2-((R)-oxiran-2-yl)-2H-chromene as a yellow oil. Separation via chomatography on silica, using heptane:ethyl acetate 9:1 as eluent, furnished 0.16 g of (R)-6-fluoro-3,4-dihydro-2-((R)-oxiran-2-yl)-2H-chromene as a colourless oil (66% yield).

NMR: $\delta_H$(400 MHz; CDCl$_3$) 6.81-6.72 (3H, m), 3.88-3.82 (1H, m), 3.21-3.17 (1H, m), 2.89-2.76 (4H, m), 2.1-2.00 (1H, m), 1.97-1.87 (1H, m).

EXAMPLE 7

Synthesis of (S)-6-fluoro-3,4-dihydro-2-((R)-oxiran-2-yl)-2H-chromene (R)-1-((S)-6-fluoro-3,4-dihydro-2H-chromen-2-yl) ethane-1,2-diol (0.27 g, 1.27 mmol) was dissolved in dichloromethane (10 ml) under nitrogen atmosphere and pyridine (510 µl) added under stirring. The reaction mixture was then cooled to 1° C. and tosyl chloride (0.24 g, 1.27 mmol) in dichloromethane (3 ml) was added over a period of 2.5 h. The reaction was quenched with saturated ammonium chloride (1 ml) and further diluted with dichloromethane (10 ml) and demi water (10 ml). The aqueous layer was separated and further extracted with dichloromethane (15 ml). The collected organic layers were dried over magnesium sulfate, filtered and concentrated in vacuo to furnish a colourless oil. Said oil was dissolved in methanol (3 ml) and dichloromethane (6 ml) under stirring in nitrogen atmosphere and potassium carbonate (0.32 g, 2.35 mmol) added. The reaction mixture was left to stir for 15 h at 25° C. The reaction was then diluted with water (10 ml) and dichloromethane (10 ml). The separated aqueous layer was further extracted with dichloromethane (20 ml). The collected organic layers were dried over magnesium sulfate and concentrated in vacuo to furnish crude (S)-6-fluoro-3,4-dihydro-2-((R)-oxiran-2-yl)-2H-chromene as a yellow oil. Separation via chomatography on silica, using heptane:ethyl acetate 9:1 as eluent, furnished 30 mg of (S)-6-fluoro-3,4-dihydro-2-((R)-oxiran-2-yl)-2H-chromene as a colourless oil (12% yield).

NMR: $\delta_H$(400 MHz; CDCl$_3$) 6.84-6.73 (3H, m), 3.87-3.81 (1H, m), 3.15-3.10 (1H, m), 2.91-2.78 (4H, m), 2.18-2.10 (1H, m), 1.96-1.84 (1H, m).

EXAMPLE 8

Synthesis of (R)-2-(benzylamino)-1-((S)-6-fluoro-3,4-dihydro-2H-chromen-2-yl)ethanol (S)-6-fluoro-3,4-dihydro-2-((R)-oxiran-2-yl)-2H-chromene (30 mg, 0.154 mmol) was dissolved in methanol (2 ml) and kept under stirring. benzylamine (40 mg, 0.374 mmol) was added and the reaction mixture left to stir. After checking the reaction outcome, the solution was concentrated under reduced pressure and the crude residue further dried at 30° C. in vacuo to furnish 30 mg of (R)-2-(phenylmethylimino)-1-((S)-6-fluoro-3,4-dihydro-2H-chromen-2-yl) ethanol as a white solid (64% yield).

LC-MS: m/z (ESI) 302 (MH$^+$, 100%);

NMR: $\delta_H$(400 MHz; CDCl$_3$) 7.37-7.27 (5H, m, Ar), 6.82-6.67 (3H, m, Ar), 3.9-3.7 (4H, m), 3.0-2.95 (1H, dd), 2.88-2.71 (3H, m), 2.18-2.09 (1H, m), 1.9-1.75 (1H, m).

EXAMPLE 9

Synthesis of [2S,αR,2'R,α'R]-α-α'-[[(phenylmethyl) imino]bismethylene]bis[6-fluoro-3,4-dihydro-2H-1-benzopyran-2-methanol]

(R)-2-(benzylamino)-1-((S)-6-fluoro-3,4-dihydro-2H-chromen-2-yl)ethanol (30 mg, 0.099 mmol) was dissolved in absolute ethanol (3 ml). Subsequently (R)-6-fluoro-3,4-dihydro-2-((R)-oxiran-2-yl)-2H-chromene (40 mg, 0.206 mmol) was added to the reaction mixture under stirring. The mixture was refluxed for 4 h and then the temperature decreased to 20° C. The crude mixture was then concentrated under reduced pressure and purified to furnish 46 mg of [2S,αR,2'R,α'R]-

α-α'-[[(phenylmethyl)imino]bismethylene]bis[6-fluoro-3,4-dihydro-2H-1-benzopyran-2-methanol] (93% yield).
LC-MS: m/z (ESI) 496 (MH+, 100%).

EXAMPLE 10

Synthesis of [2S,αR,2'R,α'R]-α-α'-[iminobismethylene]bis[6-fluoro-3,4-dihydro-2H-1-benzopyran-2-methanol] formate

[2S,αR,2'R,α'R]-α-α'-[[(phenylmethyl)imino]bismethylene]bis[6-fluoro-3,4-dihydro-2H-1-benzopyran-2-methanol] (46 mg, 0.093 mmol) was dissolved in methanol (4 ml). ammonium formate (44 mg, 0.698 mmol) was then added to the reaction mixture followed by catalytic palladium on carbon (10%). The reaction mixture was then refluxed for 11 h cooled to 25° C., filtered and concentrated in vacuo. The crude residue was then purified by inverse phase chromatography to obtain 22 mg of [2S,αR,2'R,α'R]-α-α'-[iminobismethylene]bis[6-fluoro-3,4-dihydro-2H-1-benzopyran-2-methanol] formate (52% yield).
LC-MS: m/z (ESI) 406 (MH+, 100%). Chiral HPLC: 94% ee.
NMR: $\delta_H$(400 MHz; CD$_3$OD) 8.52 (1H, s), 6.84-6.74 (6H, m), 4.12-3.89 (4H, m), 3.52-3.18 (4H, m), 2.96-2.77 (4H, m), 2.28-2.20 (1H, m), 2.05-1.86 (2H, m), 1.83-1.72 (1H, m).

EXAMPLE 11

The compound [2R,αS,2'S,α'S]-α-α'-[iminobismethylene]bis[6-fluoro-3,4-dihydro-2H-1-benzopyran-2-methanol] (1-NBV) was prepared in accordance to the procedures described in Examples 1 to 10 starting from (S)-2,2-dimethyl-1,3-dioxolane-4-carbaldehyde.

EXAMPLE 12

Synthesis of 6-fluoro-2-((R)-2,2-dimethyl-1,3-dioxolan-4-yl)-2H-chromene 1-((R)-2,2-dimethyl-1,3-dioxolan-4-yl)-prop-2-en-1-ol (0.3 g, 1.90 mmol), sodium hydrogen carbonate (0.22 g, 2.58 mmol), 2-bromo-4-fluorophenyl acetate (0.3 g, 1.29 mmol), palladium acetate (14 mg, 0.06 mmol) and CYTOP 216, 2,4,6 trioxy 1,3,5,7 tetramethyl 8 phosphaadamantane (19 mg, 0.06 mmol) were suspended in DMF (5 ml) under nitrogen. The reaction mixture was stirred at 120° C. for 19 h, cooled to 25° C. and then diluted with ethyl acetate (20 ml) and demi water (20 ml). The phases were separated and the organic layer dried over anhydrous magnesium sulfate, filtered and concentrated under vacuum to dryness. The crude reaction mixture was then purified by flash chromatography on silica (heptane:ethyl acetate 9:1) and 6-fluoro-2-((R)-2,2-dimethyl-1,3-dioxolan-4-yl)-2H-chromene was isolated as a pale yellow oil (60 mg, 19% yield).
NMR Diast SR: $\delta_H$(600 MHz; CDCl$_3$) 6.76(1H, dt, Ar, $J_{HF}$ 8.9, J 8.9, J 3.1), 6.67(1H, dd, Ar, J 8.5, $J_{HF}$ 4.5), 6.66 (1H, dd, Ar, $J_{HF}$ 9.0, J 3.0), 6.40 (1H, dd, CH=, J 10.1, J 1.9), 5.91 (1H, dd, CH=, J 10.1, J 3.2, J 0.9), 4.72 (1H, m, OCH, J 7.5, J 3.2, J 1.8), 4.27 (1H, m, OCH, J 7.5, J 6.2, J 4.9), 4.12 (1H, dd, CH$_2$O, J 8.8, J 6.2), 4.065 (1H, dd, CH$_2$O, J 8.8, J 4.9), 1.44 (3H, s, CH$_3$), 1.36 (3H, s, CH$_3$). m/z (EI) 250.10037 (M+. C$_{14}$H$_{15}$FO$_3$ requires 250.100525).
NMR Diast RR: $\delta_H$(400 MHz; CDCl$_3$) 6.79(1H, dt, Ar, $J_{HF}$ 8.9, J 8.9, J 2.8), 6.76(1H, dd, Ar, J 8.8, $J_{HF}$ 4.8), 6.67(1H, dd, Ar, $J_{HF}$ 8.8, J 2.8), 6.46 (1H, dd, CH=, J 10.0, J 1.8), 5.72(1H, dd, CH=, J 10.0, J 3.6), 4.94(1H, m, OCH, J 5.4, J 3.6, J 1.8), 4.35(1H, m, OCH, J 6.5, J 5.4), 4.06 (1H, dd, CH$_2$O, J 8.8, J 6.4), 3.97(1H, dd, CH$_2$O, J 8.8, J 6.4), 1.40 (3H, s, CH$_3$), 1.36 (3H, s, CH$_3$). m/z (EI) 250.10076 (M+. C$_{14}$H$_{15}$FO$_3$ requires 250.100525).

EXAMPLE 13

Synthesis of 6-fluoro-2-((R)-2,2-dimethyl-1,3-dioxolan-4-yl)-2H-chromene

Part A: 1-((R)-2,2-dimethyl-1,3-dioxolan-4-yl)-prop-2-en-1-ol (5.0 g, 0.0316 mol), 2-bromo-4-fluoro phenol (5.0 g, 0.0262 mol), potassium carbonate (9.0 g, 0.0652 mol), palladium acetate (290 mg, 0.0013 mol) and CYTOP 216, 2,4,6 trioxy 1,3,5,7 tetramethyl 8 phosphaadamantane (380 mg, 0.0013 mol) were added to a solvent mixture constituted by THF (10 ml) and demi water (10 ml) under nitrogen. The reaction mixture was stirred at 78° C. for 14 h, cooled to 25° C. and then diluted with ethyl acetate (50 ml) and demi water (40 ml). The organic layer was separated, dried over anhydrous magnesium sulfate, filtered and concentrated in vacuo to furnish 9.18 g of crude reaction mixture. Chromatographic purification on silica (heptane:ethyl acetate 4:1) gave a mixture of uncyclized diol XIIa 4-fluoro-2-((E/Z)-3-hydroxy-3-((R)-2,2-dimethyl-1,3-dioxolan-4-yl)-prop-1-enyl)-phenol (4.52 g, 64% yield, E/Z=86/14, Diast A/Diast B=60/40) and emiacetal XIIa 6-fluoro-3,4-dihydro-2-((R)-2,2-dimethyl-1,3-dioxolan-4-yl)-2H-chromen-2-ol (1.60 g, 23%, Diast A/Diast B=57/43).
NMR Trans Diol XIIa (E): $\delta_H$(400 MHz; CDCl$_3$) 7.04-6.98 (2H, m), 6.93-6.76 (4H, m, Ar), 6.73-6.68 (2H, m, Ar), 6.21-6.09 (2H, m), 6.00-5.90 (2H, b), 4.48-4.42 (1H, b), 4.28-4.22 (1H, b), 4.25-4.18 (2H, m), 4.05-3.94 (3H, m), 3.88-3.83 (1H, m), 2.63 (1H, s), 2.05 (1H, s), 1.48 (3H, s), 1.47 (3H, s), 1.38 (6H, s); LC-MS: m/z (ESI) 291.1 (MNa+).
NMR Emiacetal XIIa: $\delta_H$(400 MHz; CDCl$_3$) 6.84-6.74 (6H, m, Ar), 4.29-4.25 (1H, m), 4.21-4.10 (4H, m), 3.9-3.85 (1H, m), 3.40 (1H, d, J 2), 3.16 (1H, d, J 2), 3.13-3.00 (2H, m), 2.73-2.65 (2H, m), 2.11-2.03 (1H, m), 1.89-1.83 (1H, m), 1.78-1.69 (2H, m), 1.55 (3H, s), 1.51 (3H, s), 1.47 (3H, s), 1.42 (3H, s); m/z (EI) 268.11135 (M+. C$_{14}$H$_{17}$FO$_4$ requires 268.11109).
Part B: 4-Fluoro-2-((E/Z)-3-hydroxy-3-((R)-2,2-dimethyl-1,3-dioxolan-4-yl)-prop-1-enyl)-phenol was submitted to the zinc chloride cyclization step.
Zinc chloride (0.85 g, 6.21 mmol) and lithium chloride (0.37 g, 8.73 mmol), were suspended in toluene under nitrogen atmosphere. The vigorously stirred slurry was refluxed and water separated by azeotropic distillation. To the dry toluene mixture, catalytic tetrabutyl ammonium chloride was added, followed by a solution of 4-fluoro-2-((E/Z)-3-hydroxy-3-((R)-2,2-dimethyl-1,3-dioxolan-4-yl)-prop-1-enyl)-phenol (1.0 g, 3.73 mmol) in toluene (4.8 g). After 3 h heating, the heterogeneous reaction mixture was cooled to 25° C. and the solid residue filtered and washed with toluene (5 ml). The organic phase was concentrated to dryness under reduced pressure at 45° C. to give 6-fluoro-2-((R)-2,2-dimethyl-1,3-dioxolan-4-yl)-2H-chromene (0.16 g, 17%) as a 64:36 mixture of distereoisomers.
NMR Diast SR: $\delta_H$(600 MHz; CDCl$_3$) 6.76(1H, dt, Ar, $J_{HF}$ 8.9, J 8.9, J 3.1), 6.67(1H, dd, Ar, J 8.5, $J_{HF}$ 4.5), 6.66 (1H, dd, Ar, $J_{HF}$ 9.0, J 3.0), 6.40 (1H, dd, CH=, J 10.1, J 1.9), 5.91 (1H, dd, CH=, J 10.1, J 3.2, J 0.9), 4.72 (1H, m, OCH, J 7.5, J 3.2, J 1.8), 4.27 (1H, m, OCH, J 7.5, J 6.2, J 4.9), 4.12 (1H, dd, CH$_2$O, J 8.8, J 6.2), 4.065 (1H, dd, CH$_2$O, J 8.8, J 4.9), 1.44 (3H, s, CH$_3$), 1.36 (3H, s, CH$_3$). m/z (EI) 250.10037 (M+. C$_{14}$H$_{15}$FO$_3$ requires 250.100525).

NMR Diast RR: $\delta_H$(400 MHz; CDCl$_3$) 6.79(1H, dt, Ar, $J_{HF}$ 8.9, J 8.9, J 2.8), 6.76(1H, dd, Ar, J 8.8, $J_{HF}$ 4.8), 6.67(1H, dd, Ar, $J_{HF}$ 8.8, J 2.8), 6.46 (1H, dd, CH=, J 10.0, J 1.8), 5.72(1H, dd, CH=, J 10.0, J 3.6), 4.94(1H, m, OCH, J 5.4, J 3.6, J 1.8), 4.35(1H, m, OCH, J 6.5, J 5.4), 4.06 (1H, dd, CH$_2$O, J 8.8, J 6.4), 3.97(1H, dd, CH$_2$O, J 8.8, J 6.4), 1.40 (3H, s, CH$_3$), 1.36 (3H, s, CH$_3$). m/z (EI) 250.10076 (M$^+$. C$_{14}$H$_{15}$FO$_3$ requires 250.100525).

EXAMPLE 14

Synthesis of 6-fluoro-3,4-dihydro-2-((R)-2,2-dimethyl-1,3-dioxolan-4-yl)-2H-chromene A 75:25 diastereoisomeric mixture of 6-fluoro-2-((R)-2,2-dimethyl-1,3-dioxolan-4-yl)-2H-chromene (50 mg, 0.18 mmol, 90.4% A) was dissolved in ethanol and stirred under nitrogen athmosphere at 25° C. Ammonium formiate (60.5 mg, 0.96 mmol) and 10% palladium on carbon (50 mg) were added to the stirred solution and the reaction mixture refluxed for 15 h. The reaction mixture was checked to show complete conversion of the starting material. The solids were removed by filtration and the filtrate was concentrated under reduced pressure to furnish 6-fluoro-3,4-dihydro-2-((R)-2,2-dimethyl-1,3-dioxolan-4-yl)-2H-chromene (40 mg, 0.115 mmol, 72.6% A, 64% yield) as a 75:25 mixture of diastereoisomers.

NMR Diast. RR: $\delta_H$(400 MHz; CDCl$_3$) 6.81-6.72 (3H, m, Ar), 4.32-4.28 (1H, m), 4.10 (1H, dd, J 7, 7), 4.02 (1H, dddd, J 11, 6, 2), 3.91 (1H, dd, J 7, 7), 2.91-2.72 (2H, m), 1.96-1.74 (2H, m), 1.46 (3H, s), 1.41 3H, s).

NMR Diast. SR: $\delta_H$(400 MHz; CDCl$_3$) 6.81-6.70 (3H, m, Ar), 4.19 (1H, dd, J 8, 6), 4.14-4.10 (1H, m), 4.06 (1H, dd, J 8, 5), 3.88 (1H, ddd, J 10, 7, 2.3), 2.88-2.72 (2H, m), 2.26-2.18 (1H, m), 1.83-1.73 (1H, m), 1.45 (3H, s), 1.39 (3H, s); m/z (EI) 252.1139 (M$^+$. C$_{14}$H$_{17}$FO$_3$ requires 252.1157).

EXAMPLE 15

Synthesis of (R)-1-(6-fluoro-3,4-dihydro-2H-chromen-2-yl)-ethane-1,2-diol

6-Fluoro-3,4-dihydro-2-((R)-2,2-dimethyl-1,3-dioxolan-4-yl)-2H-chromene (40 mg, 0.16 mmol, diastereomeric ratio 75:25) was dissolved in acetic acid (2 ml) and demi water (0.7 ml). The reaction mixture was stirred vigorously and heated to 65° C. After 3 h at 65° C. the reaction mixture was cooled to 25° C. The solution was then concentrated in vacuo at 35° C. to obtain (R)-1-(6-fluoro-3,4-dihydro-2H-chromen-2-yl)-ethane-1,2-diol as a vetrous oil (89% yield, diastereomeric ratio 73:27).

NMR Diast RR: $\delta_H$(400 MHz; CDCl$_3$) 6.82-6.73 (3H, m), 4.10-4.03 (1H, m), 3.89-3.75 (3H, m), 2.93-2.74 (2H, m), 2.65 (1H, b), 2.10 (1H, b), 2.04-1.90 (2H, m).

NMR Diast SR: $\delta_H$(400 MHz; CDCl$_3$) 6.83-6.69 (3H, m, Ar), 4.05-3.98 (1H, m), 3.90-3.80 (3H, m), 2.91-2.74 (2H, m), 2.18-2.11 (1H, m), 1.91-1.81 (1H, m). Chiral HPLC: ee 78%.

The invention claimed is:
1. A process for preparing d-NBV of formula

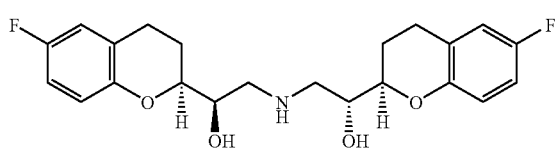

(IA)

which comprises:

a) reacting 2,2-dimethyl-1,3 dioxolane-4-carbaldehyde of formula

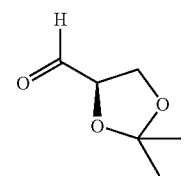

Ia with a vinyl Grignard reagent, to obtain a compound of formula IIa in the form of diastereoisomeric mixture (S,R+R,R)

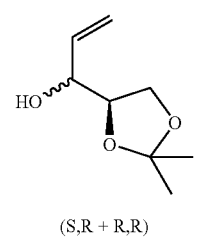

IIa b) reacting the above compound of formula IIa with 2-bromo-4-fluorophenol to obtain a compound of formula IIIa in the form of diastereoisomeric mixture (S,R+R,R)

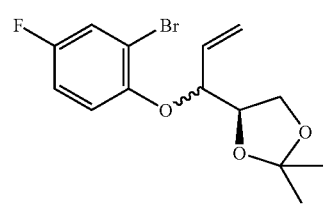

IIIa c) reacting the compound of the above formula IIIa with an organoborane compound of formula

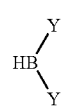

IIIc wherein each Y is a siamyl group, an isopropyl-prenyl group, a cyclohexyl group, an isopinocampheyl group and a thexyl group;

or both Y taken together with the boron atom to which they are linked form a borabicyclo[3.3.1]non-9-yl group or a residue of formula:

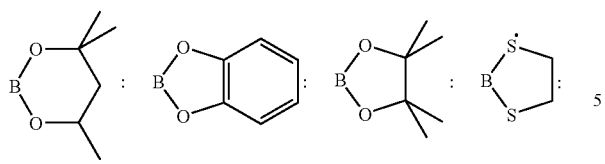 : 5 to obtain a compound of formula IVa in the form of diastereoisomeric mixture (S,R+R,R)

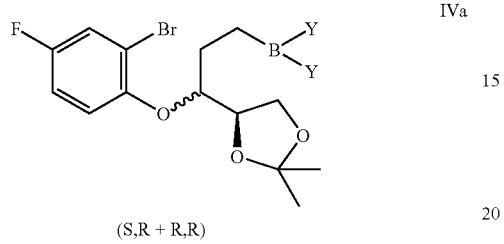

IVa (S,R + R,R)

wherein
Y is defined above;

d) cyclizing the above compound of formula IVa to obtain a compound of formula Va in the form of diastereoisomeric mixture (S,R+R,R)

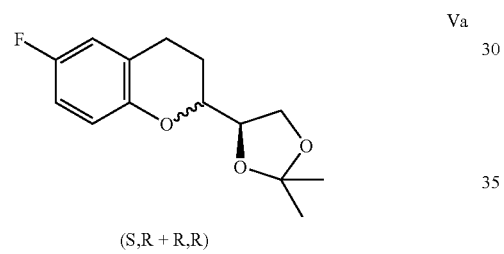

Va (S,R + R,R)

and, if desired, separating the compound of formula Va (S,R+R,R) into the single diastereomer Va (S,R) and the single diastereomer Va (R,R);

e) hydrolysing the diastereoisomeric mixture of formula Va (S,R+R,R) or, alternatively, hydrolysing separately the diastereomer Va (S,R) and the diastereomer Va (RR), to obtain the corresponding diastereoisomeric mixture of formula VIa (S,R+R,R)

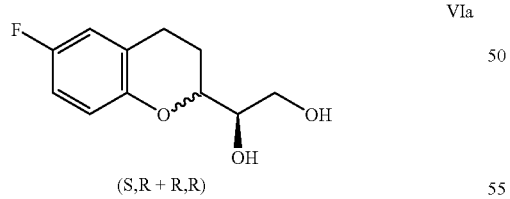

VIa (S,R + R,R)

or, independently, the diastereomer VIa (S,R)

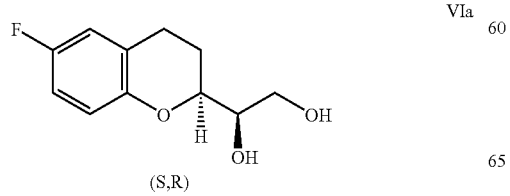

VIa (S,R)

and the diastereomer VIa (RR)

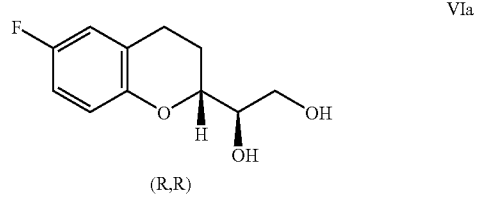

VIa (R,R)

f) reacting the diastereoisomeric mixture of formula VIa (S,R+R,R), or alternatively reacting separately the diastereomer VIa (S,R) and the diastereomer VIa (R,R) with a reactant able to introduce a good leaving group to obtain the corresponding diastereoisomeric mixture of formula VIIa (S,R+R,R)

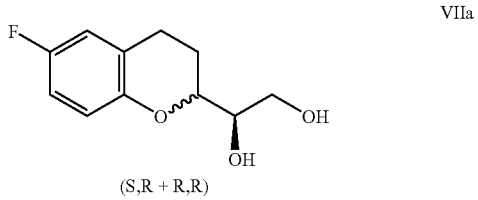

VIIa (S,R + R,R)

or, independently, the diastereomer VIIa (S,R)

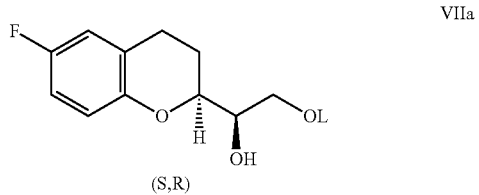

VIIa (S,R)

and the diastereomer VIIa (R,R)

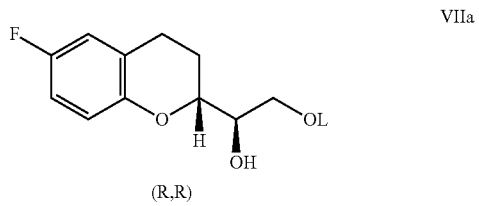

VIIa (R,R)

wherein
L is tosyl or mesyl;

g) reacting the diastereoisomeric mixture of formula VIIa (S,R+R,R), or alternatively reacting separately the diastereomer VIIa (S,R) and the diastereomer VIIa (R,R) with a base to obtain the corresponding diastereoisomeric mixture of formula VIIIa (S,R+R,R)

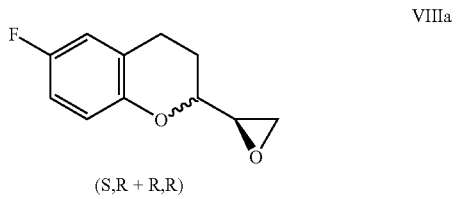

VIIIa (S,R + R,R)

or, independently, the diastereomer VIIa (S,R)

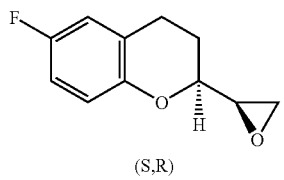

(S,R) VIIIa and the diastereomer VIIIa (R,R)

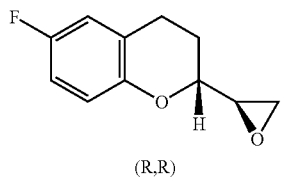

(R,R) VIIIa and separating, if the case, the diastereoisomeric mixture of formula VIIIa (S,R+R,R) into the single diastereomer VIIIa (S,R) and the single diastereomer VIIIa (R,R);

h) reacting separately the compound of formula VIIIa (S,R) or the compound of formula VIIIa (R,R) with a protected $H_2N$-P amine wherein P is a nitrogen protecting group, to obtain a compound of formula IXa (S,R) or a compound of formula IXa (R,R)

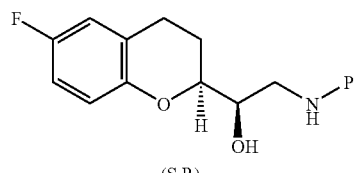

(S,R) IXa

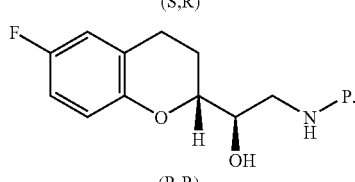

(R,R) IXa i) reacting the compound of formula IXa (S,R) or the compound of formula IXa (R,R) with a compound of formula VIIIa (R,R) or a compound VIIIa (S,R) respectively, to obtain a compound of formula Xa (S,R,R,R) or a compound Xa (R,R,R,S), being the compound of formula Xa (S,R,R,R) the same stereoisomer of the compound Xa (R,R,R,S), because of the presence in the structure of compound Xa of an axis of symmetry which contains the nitrogen atom

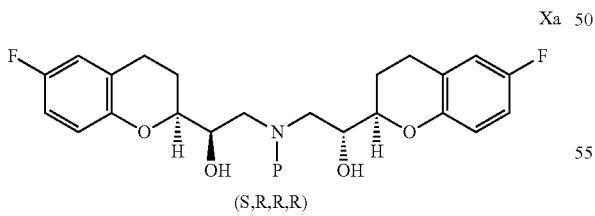

(S,R,R,R) Xa i.e.

j)

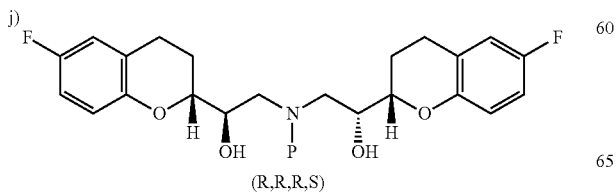

(R,R,R,S) Xa deprotecting the compound of formula Xa to give d-NBV of the above formula IA;

k) and, if desired, salifying the compound of formula IA.

2. A process for preparing l-NBV of formula

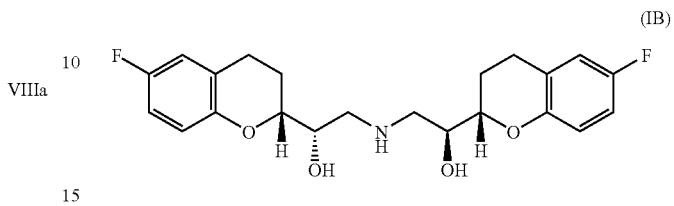

(IB)

which comprises:

1) reacting 2,2-dimethyl-1,3 dioxolane-4-carbaldehyde of formula

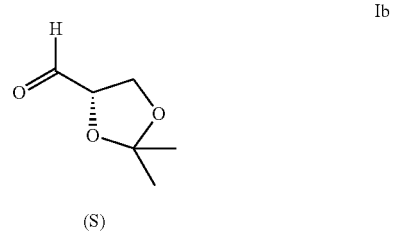

(S) Ib with a vinyl Grignard reagent to obtain a compound of formula IIb in the form of diastereoisomeric mixture (R,S+S,S)

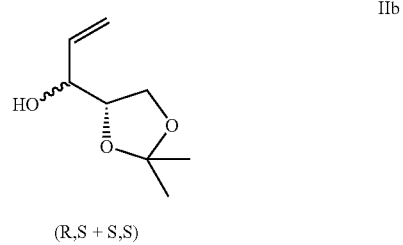

(R,S + S,S) IIb m) reacting the above compound of formula IIb with 2-bromo-4-fluorophenol to give a compound of formula IIIb in the form of diastereoisomeric mixture (R,S+S,S)

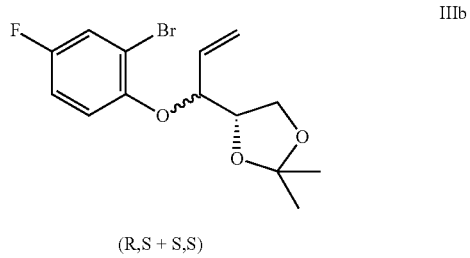

(R,S + S,S) IIIb n) reacting the compound of the above formula IIIb with an organoborane compound of formula

IIIc wherein Y is as defined in claim 1; to obtain a compound of formula IVb in the form of diastereoisomeric mixture (R,S+S,S)

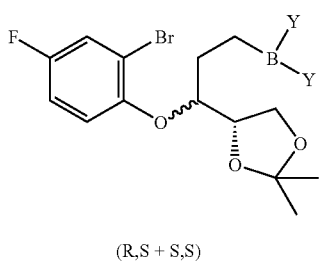

IVb (R,S + S,S)

wherein Y is defined above;

o) cyclizing the above compound of formula IVb to obtain a compound of formula Vb in the form of diastereoisomeric mixture (R,S+S,S)

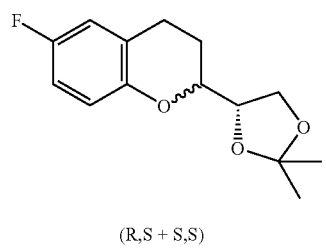

Vb (R,S + S,S)

and, if desired, separating the compound of formula Vb (R,S+S,S) into the single diastereomer Vb (R,S) and the single diastereomer Vb (S,S);

p) hydrolysing the diastereoisomeric mixture of formula Vb (R,S+S,S) or, alternatively, hydrolysing separately the diastereomer Vb (R,S), and the diastereomer Vb (S,S) to obtain the corresponding diastereoisomeric mixture of formula VIb (R,S+S,S)

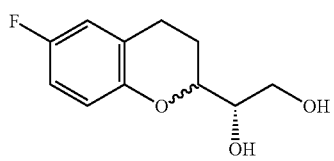

VIb (R,S + S,S)

or, independently, the diastereomer VIb (R,S)

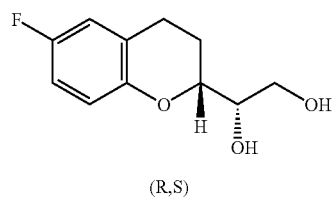

VIb (R,S)

and the diastereomer VIb (S,S)

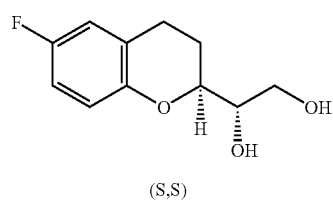

VIb (S,S)

q) reacting the diastereoisomeric mixture of formula VIb (R,S+S,S) or, alternatively, reacting separately the diastereomer VIb (R,S) and the diastereomer VIb (S,S) with a reactant able to introduce a good leaving group, to obtain the corresponding diastereoisomeric mixture of formula VIIb (R,S+S,S)

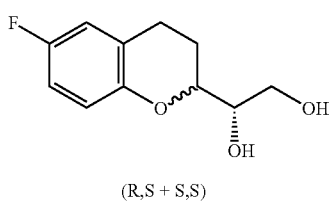

VIIb (R,S + S,S)

or, independently, the diastereomer VIIb (R,S)

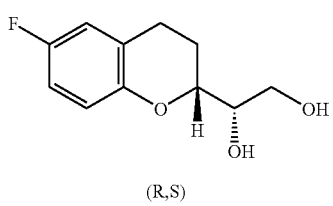

VIIb (R,S)

and the diastereomer VIIb (S,S)

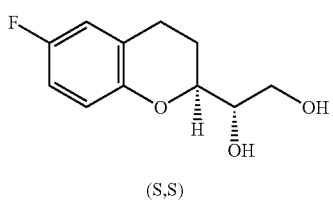

VIIb (S,S)

wherein
L is defined above r) reacting the diastereoisomeric mixture of formula VIIb (R,S+S,S), or, alternatively, reacting separately the diastereomer VIIb (R,S) and the diastereomer VIIb (S,S)

with a base to give the corresponding diastereoisomeric mixture of formula VIIIb (R,S+S,S)

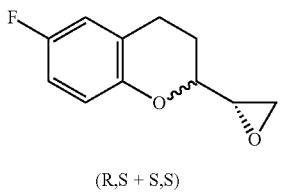

(R,S + S,S)

VIIIb or, independently, the diastereomer VIIb (R,S)

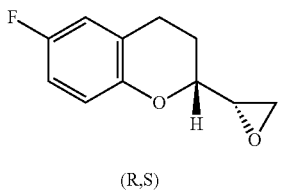

(R,S)

VIIIb and the diastereomer VIIb (S,S)

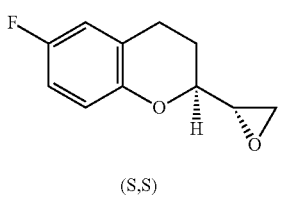

(S,S)

VIIIb and separating, if the case, the diastereoisomeric mixture of formula VIIIb (R,S+S,S) into the single diastereomer VIIIb (R,S) and the single diastereomer VIIIb (S,S);

s) reacting separately the compound of formula VIIIb (R,S) or the compound of formula VIIIb (S,S) with a protected H₂N-P amine wherein P is a nitrogen protecting group to give a compound of formula IXb (R,S)

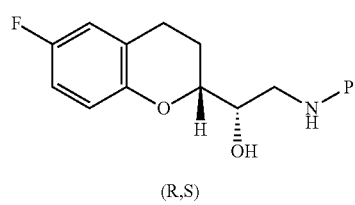

(R,S)

IXb or a compound of formula IXb (S,S)

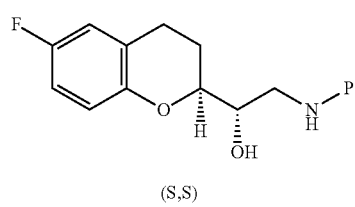

(S,S)

IXb t) reacting the compound of formula IXb (R,S) or the compound of formula IXb (S,S) with a compound of formula VIIIb (S,S) or a compound VIIIb (R,S) respectively, to obtain a compound of formula Xb (R,S,S,S) or a compound Xb (S,S,S,R), being the compound of formula Xb (R,S,S,S) the same stereoisomer of the compound Xb (S,S,S,R), because of the presence in the structure of compound Xb of an axis of symmetry which contains the nitrogen atom

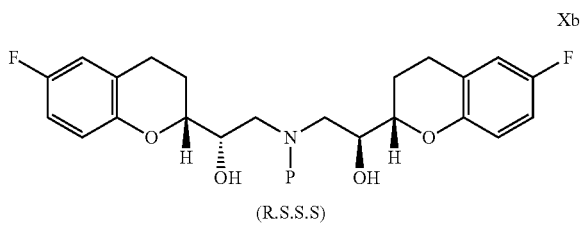

(R.S.S.S)

Xb i.e.

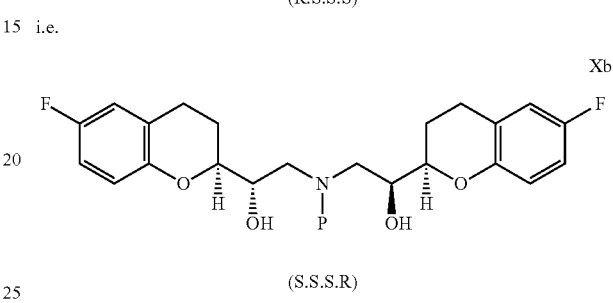

(S.S.S.R)

Xb u) deprotecting the compound of formula Xb to give l-NBV of the above formula IB;
v) and, if desired, salifying the compound of formula IB.

3. A process for preparing d-NBV of formula IA which comprises reaction steps from a) to d) as defined in claim 1 to give a compound of formula

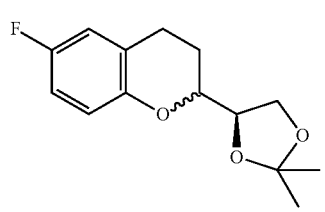

(S,R + R,R)

Va in the form of diastereoisomeric mixture (S,R+RR) and optionally separating said compound of formula Va (S,R+R,R) into the single diastereomer Va (S,R) and the single diastereomer Va (R,R).

4. A process for preparing l-NBV of formula IB which comprises reaction steps from 1) to o) as defined in claim 2 to give a compound of formula

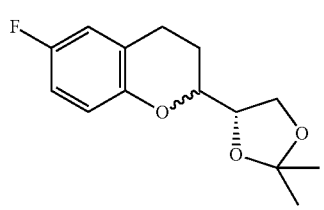

(R,S + S,S)

Vb in the form of diastereoisomeric mixture (R,S+S,S) and optionally separating said compound of formula Vb (R,S+S,S) into the single diastereomer Vb (R,S) and the single diastereomer Vb (S,S).

5. A process according to claim 1 wherein step a is carried out by reacting a compound of formula Ia with vinyl magnesium bromide or vinyl magnesium chloride to give a compound of formula IIa in the form of diastereomeric mixture.

6. A process according to claim 1 wherein step b is carried out by reacting a compound of formula IIa with 2-bromo-4-fluorophenol in the presence of a phosphine and an aza compound under Mitsunobu conditions to give a compound of formula IIIa in the form of diastereomeric mixture.

7. A process according to claim 6 wherein the phosphine is triphenylphosphine or tri-n-butylphosphine.

8. A process according to claim 6 wherein the aza compound is selected from DIAD, DEAD and ADDP.

9. A process according to claim 1 wherein step c is carried out by reacting a compound of formula IIIa with 9-borabicyclo[3.3.1]nonane to give a compound of formula IVa in the form of diastereomeric mixture.

10. A process according to claim 1 wherein step d is carried out by reacting a compound of formula IVa with a base in the presence of a palladium catalyst under B-alkyl Suzuki conditions to give a compound of formula Va in the form of diastereomeric mixture.

11. A process according to claim 10 further comprising separating a compound of formula Va in the form of diastereomeric mixture into the single diastereomer Va (S,R) and the single diastereomer Va (R,R).

12. A process according to claim 10 wherein the base is a mineral base or an amine.

13. A process according to claim 10 wherein the palladium catalyst is a ligandless palladium catalyst or a palladium complex catalyst.

14. A process according to claim 10 wherein the amount of catalyst is comprised between around 0.01 and 10 mol %.

15. A compound of formula:
(S)-4-(1-((R,S)-2-bromo-4-fluorophenoxy)-allyl)-2,2-dimethyl-1,3-dioxolane;
(R)-4-(1-((R,S)-2-bromo-4-fluorophenoxy)-allyl)-2,2-dimethyl-1,3-dioxolane;
(S)-4-(1-((R,S)-2-bromo-4-fluorophenoxy)-3-(borabicyclo[3.3.1]non-9-yl)-propyl)-2,2-dimethyl-1,3-dioxolane;
(R)-4-(1-((R,S)-2-bromo-4-fluorophenoxy)-3-(borabicyclo[3.3.1]non-9-yl)-propyl)-2,2-dimethyl-1,3-dioxolane.

16. (±)[R*,S*,S*,S*]-α-α'-[iminobismethylene]bis[6-fluoro-3,4-dihydro-2H-1-benzopyran-2-methanol] formate.

17. [2S,αR,2'R,α'R]-α-α'-[iminobismethylene]bis[6-fluoro-3,4-dihydro-2H-1-benzopyran-2-methanol] formate.

18. [2R,αS,2'S,α'S]-α-α'-[iminobismethylene]bis[6-fluoro-3,4-dihydro-2H-1-benzopyran-2-methanol] formate.

19. A process according to claim 2 wherein step l is carried out by reacting a compound of formula Ib with vinyl magnesium bromide or vinyl magnesium chloride to give a compound of formula IIb in the form of diastereomeric mixture.

20. A process according to claim 2 wherein step m is carried out by reacting a compound of formula IIb with 2-bromo-4-fluorophenol in the presence of a phosphine and an aza compound under Mitsunobu conditions to give a compound of formula IIIb in the form of diastereomeric mixture.

21. A process according to claim 20 wherein the phosphine is triphenylphosphine or tri-n-butylphosphine.

22. A process according to claim 20 wherein the aza compound is selected from DIAD, DEAD and ADDP.

23. A process according to claim 2 wherein step n is carried out by reacting a compound of formula IIIb with 9-borabicyclo[3.3.1]nonane to give a compound of formula IVb in the form of diastereomeric mixture.

24. A process according to claim 2 wherein step o is carried out by reacting a compound of formula IVb with a base in the presence of a palladium catalyst under B-alkyl Suzuki conditions to give a compound of formula Vb in the form of diastereomeric mixture.

25. A process according to claim 24 further comprising separating a compound of formula Vb in the form of diastereomeric mixture into the single diastereomer Vb (R,S) and the single diastereomer Vb (S,S).

26. A process according to claim 24 wherein the base is a mineral base or an amine.

27. A process according to claim 24 wherein the palladium catalyst is a ligandless palladium catalyst or a palladium complex catalyst.

28. A process according to claim 24 wherein the amount of catalyst is comprised between around 0.01 and 10 mol %.

\* \* \* \* \*